United States Patent
Ma et al.

(10) Patent No.: US 9,437,628 B1
(45) Date of Patent: Sep. 6, 2016

(54) BIODEGRADABLE MICROWAVE ELECTRONIC DEVICES

(71) Applicant: Wisconsin Alumni Research Foundation, Madison, WI (US)

(72) Inventors: Zhenqiang Ma, Middleton, WI (US); Yei Hwan Jung, Madison, WI (US); Shaoqin Gong, Middleton, WI (US); Tzu-Hsuan Chang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/709,850

(22) Filed: May 12, 2015

(51) Int. Cl.
   *H01L 29/00* (2006.01)
   *H01L 21/8234* (2006.01)
   *H01L 21/8244* (2006.01)
   *H01L 27/13* (2006.01)
   *H01L 21/84* (2006.01)

(52) U.S. Cl.
   CPC .............. *H01L 27/13* (2013.01); *H01L 21/84* (2013.01)

(58) Field of Classification Search
   CPC ............................ H01L 27/13; H01L 21/84
   USPC .......................................... 257/528; 438/238
   See application file for complete search history.

(56) References Cited

U.S. PATENT DOCUMENTS

| | | |
|---|---|---|
| 6,481,631 B1 | 11/2002 | Poustis |
| 2014/0130710 A1* | 5/2014 | Laukkanen .......... C09D 101/02 106/203.3 |
| 2015/0144380 A1* | 5/2015 | Yang .................... H05K 1/097 174/253 |

OTHER PUBLICATIONS

Sabo et al., Cellulose Nanofiber Composite Substrates for Flexible Electronics, A Conference Proceeding from 2012 TAPPI International Conference on Nanotechnology for Renewable Materials, Montreal, Quebec, Canada, Jun. 4, 2012.
Kuzuhara et al., GaAs-based high-frequency and high-speed devices, JSAP International No. 7, Jan. 2003, pp. 4-11.
Kim et al., An Inkjet-Printed Solar-Powered Wireless Beacon on Paper for Identification and Wireless Power Transmission Applications, IEEE Transactions on Microwave Theory and Techniques, vol. 60, No. 12, Dec. 2012, pp. 4178-4186.
Alimenti et al., 24 GHz Single-Balanced Diode Mixer Exploiting Cellulose-Based Materials, IEEE Microwave and Wireless Components Letters, vol. 23, No. 11, Sep. 5, 2013, pp. 596-598.
Orecchini et al., Design and fabrication of ultra-low cost radio frequency identification antennas and tags exploiting paper substrates and inkjet printing technology, Published in IET Microwaves, Antennas & Propagation, vol. 5, Iss. 8, 2011, pp. 993-1001.
Zheng et al., Nanostructured paper for flexible energy and electronic devices, MRS Bulletin vol. 38, Apr. 2013, pp. 320-325.
Yang et al., RFID Tag and RF Structures on a Paper Substrate Using Inkjet-Printing Technology, IEEE Transactions on Microwave Theory and Techniques, vol. 55, No. 12, Dec. 2007, pp. 2894-2901.

(Continued)

*Primary Examiner* — David S Blum
(74) *Attorney, Agent, or Firm* — Bell & Manning, LLC

(57) ABSTRACT

Substantially biodegradable microwave integrated circuits and method for making the microwave integrated circuits are provided. The integrated circuits, which have applications in high performance flexible microwave and digital electronics, utilize biobased, biodegradable cellulose nanofibril films as a substrate and comprise only very small amounts of potentially toxic inorganic materials.

17 Claims, 32 Drawing Sheets

(56) References Cited

OTHER PUBLICATIONS

Rida et al., Conductive Inkjet-Printed Antennas on Flexible Low-Cost Paper-Based Substrates for RFID and WSN Applications, IEEE Antennasand Propagation Magazine, vol. 51, No. 3, Jun. 2009, pp. 13-23.

Wu et al., Towards Practical Application of Paper based Printed Circuits: Capillarity Effectively Enhances Conductivity of the Thermoplastic Electrically Conductive Adhesives, Scientific Reports | 4 : 6275, Sep. 3, 2014, pp. 1-8.

Alimenti et al., Microwave Circuits in Paper Substrates Exploiting Conductive Adhesive Tapes, IEEE Microwave and Wireless Components Letters, vol. 22, No. 12, Dec. 2012, pp. 660-662.

CarboThermTM Boron Nitride fillers for thermoplastic polymers Novel solutions with thermally-conductive, electrically-insulating compounds, San Gobain Technical Bulletin, available on the web before May 12, 2015.

X-Celeprint, http://www.x-celeprint.com/about-us/, available on the web before May 12, 2015.

Sabo et al., Coatings, Films, and Optical Uses, Chapter 2.3 from Production and Application of Cellulose Nanomaterials, TAPPI Press (2013), pp. 263-264.

Zhang et al., Fast flexible electronics using transferrable silicon nanomembranes, Journal of Physics D: Applied Physics, vol. 45, No. 14, Mar. 23, 2012.

Sun et al., Flexible high-frequency microwave inductors and capacitors integrated on a polyethylene terephthalate substrate, Appl. Phys. Lett. 96, 013509, 2010.

Lee et al., LEGO-like assembly of peelable, deformable components for integrated devices, NPG Asia Materials 5, e66, Oct. 11, 2013.

* cited by examiner

BIODEGRADABLE MICROWAVE ELECTRONIC DEVICES

REFERENCE TO GOVERNMENT RIGHTS

This invention was made with government support under FA9550-09-1-0482 awarded by the USAF/AFOSR. The government has certain rights in the invention.

BACKGROUND

Consumer electronics, such as cell phones, tablets and other portable electronic devices, are typically made of non-renewable, non-biodegradable, and sometimes potentially toxic materials. These consumer electronics are frequently discarded, leading to serious environmental contamination. Thus, electronic systems made of renewable and biodegradable materials and minimal amount of potentially toxic materials are desirable.

The use of biodegradable materials in electronics can reduce the accumulation of persistent solid waste, thereby benefiting the environment. In order to minimize the usage of non-biodegradable semiconductors, fully formed electronic devices have been fabricated on biodegradable flexible substrates. For example, electronic devices made from organic semiconductors on paper substrates have been reported. However, the performance of such electronics does not meet the requirements for state-of-the-art electronics. In addition, electronics that include cellulose nanofibril (CNF) substrates have been reported. However, microwave-based consumer electronic devices, which require exacting radio frequency (RF) properties have not previously been reported on cellulose nanofibril substrates.

SUMMARY

Substantially biodegradable microwave integrated circuits and method for making the microwave integrated circuits are provided.

One embodiment of a microwave integrated circuit comprises: microwave integrated circuitry comprising active components and passive components, wherein at least one of the active components comprises a Group III-V semiconductor; and a biodegradable, dielectric integrated circuit substrate in contact with one or more of the active and passive components; wherein the integrated circuit substrate comprises an optically transparent film comprising cellulose nanofibrils and a hydrophobic polymer coating.

One embodiment of a method of making a microwave integrated circuit comprises the steps of: forming passive and active components for a microwave integrated circuit on one or more non-biodegradable substrates, wherein at least one of the active components comprises a Group III-V semiconductor; releasing the passive and active components from the one or more non-biodegradable substrates; and transferring the passive and active components onto a biodegradable, dielectric integrated circuit substrate, such that the passive and active components form the integrated circuitry of the microwave integrated circuit; wherein the biodegradable, dielectric integrated circuit substrate comprises an optically transparent film comprising cellulose nanofibrils and a hydrophobic polymer coating.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

DETAILED DESCRIPTION

Figure 1:
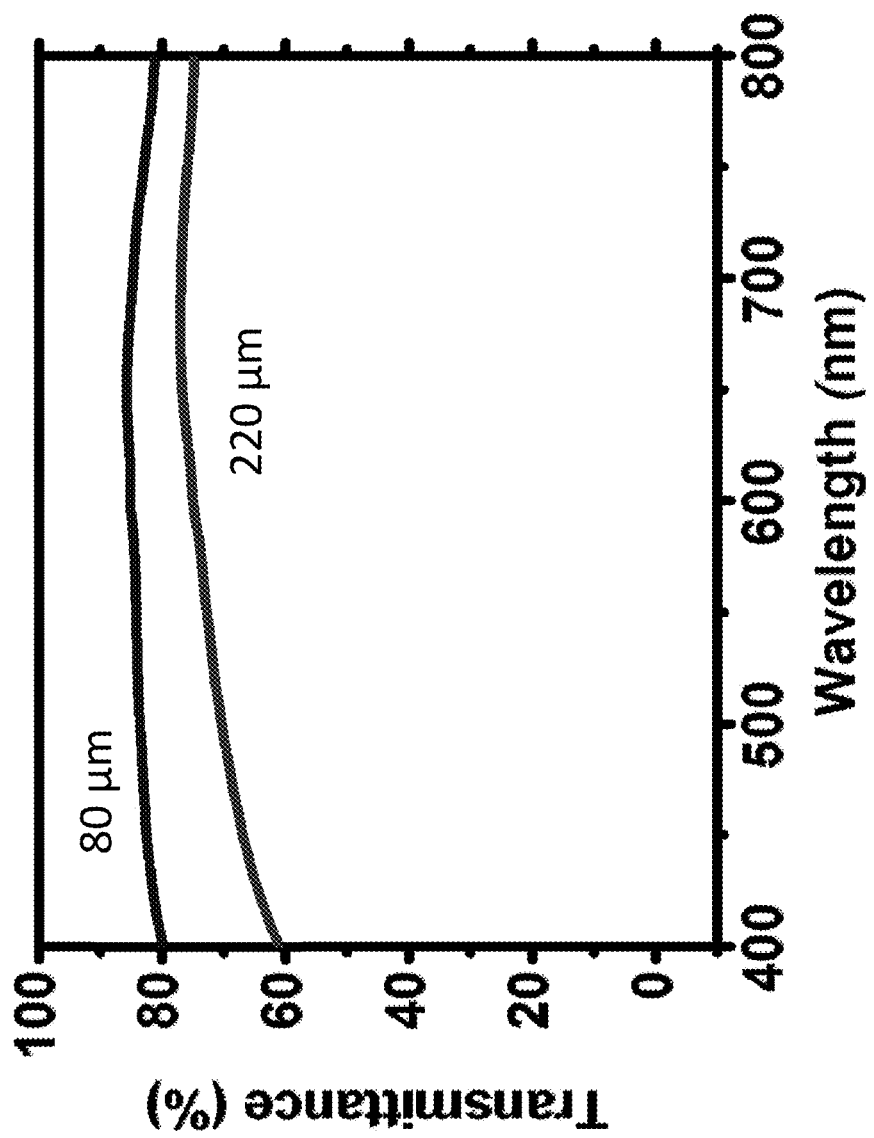
FIG. 1. The transmittance curve of a CNF substrate over a visible spectrum. Upper and lower curves show the transmittance of 80 μm and 200 μm thick CNF films, respectively.

Substantially biodegradable microwave integrated circuits and method for making the microwave integrated circuits are provided.

The integrated circuits, which have applications in high performance flexible microwave and digital electronics, utilize biobased, biodegradable CNF films as a substrate and comprise only very small amounts of potentially toxic inorganic materials. As a result, disposal of the microwave integrated circuits creates less environmentally unfriendly waste. This is particularly important for microwave devices based on gallium arsenide (GaAs) substrates.

GaAs is a toxic semiconductor that is widely used in high speed communication devices, such as cell phones and tablets, and can lead to a significant amount of hazardous materials and high cost in applications that require sparse areal coverage, such as monolithic microwave integrated circuits (MMIC). Unfortunately, the chemical extraction of GaAs from discarded waste is prohibitively expensive and dangerous due to the presence of arsenic. By replacing the GaAs substrate in such devices with a biodegradable substrate, the present microwave integrated circuits provide a substantial reduction in microwave electronics-derived arsenic waste.

The substantially biodegradable microwave integrated circuits comprise microwave integrated circuitry on an integrated circuit substrate. The integrated circuitry comprises both active components and passive components. At least one of the active components comprises a Group III-V semiconductor. The integrated circuit substrate, which is in direct contact with the integrated circuitry, comprises a cellulose nanofibril film coated with a hydrophobic polymer. The integrated circuit substrates are dielectric substrates characterized by low RF loss tangents.

The microwave integrated circuits are electronic devices that operate in the microwave regime and, therefore, the integrated circuitry of the microwave integrated circuits comprises one or more electronic components that transmit or receive an electromagnetic signal having frequencies in the range from 300 MHz to 300 GHz. Active components in the integrated circuitry can include transistors, such as bipolar transistors, and diodes, such as Schottky diodes. Passive components can include resistors, capacitors, inductors and interconnects. Combinations of these active and passive components can be combined to provide various types of integrated circuits, including microwave rectifier circuits and microwave amplifier circuits.

The active components may be based on group III-V semiconductor materials, such as doped or undoped GaAs, GaInP, or InP. However, at least some of the active components may also be based on group IV semiconductors, such as doped or undoped C, Si, Ge and/or SiGe alloys.

In some embodiments of the microwave integrated circuits, some or all of the active and/or passive components that make up the integrated circuitry are encapsulated in a coating of a substantially water insoluble polymer coating. Humidity, moisture and extreme environmental conditions affect the performance and long term reliability of electronics due to corrosion, stress, and the like. The reliability of semiconductor based devices largely depends on the moisture resistance of the plastic resin package. The substantially water insoluble polymer coatings help to prevent or minimize leakage of harmful materials, such as arsenic, from the active and/or passive components of the circuitry into the environment while the CNF substrates undergo biodegradation. In addition, by keeping the active and/or passive components of the microwave integrate circuits intact, they make it easier to collect those components for subsequent recycling after the substrate has degraded. The substantially water insoluble polymer coatings may be comprised of a variety of thermoset resins or thermoset resin blends. Examples of these include polyimide resins, epoxy resins, phenolic resins, polyurethane resins, and the like. Polyimide homo- and co-polymers are specific examples of substantially insoluble polymer coatings that can be used to encapsulate the circuitry components.

The CNF substrate (also referred to as a CNF film) comprises, consists essentially of, or consists of a mat of pressed cellulose nanofibrils and a coating of a hydrophobic polymer that encapsulates the mat. (Descriptions of Cellulose nanofibrils can be found in Zhu, et al., *Energy Environ. Sci.* 7, 269-287 (2014) and Nogi et al., *Adv. Mater.* 20, 1849-1852 (2008).) Cellulose nanofibrils are ecofriendly, as they are completely derived from wood. Thermoset resins, including polyimide resins, epoxy resins, phenolic resins, polyurethane resins, and the like, may be used as the hydrophobic polymer coating. Bisphenol A-based epoxy resins are specific examples of hydrophobic polymer coatings that can be used to encapsulate the CNF mat of the CNF substrate. The hydrophobic coating is a minority component of the substrates by weight, typically comprising no greater than about 20 wt. % of the substrate and, more desirably, no greater than about 15 wt. % of the substrate, and still more desirably, no greater than about 20 wt. % of the substrate. As a result, the substrates may comprise at least 75 wt. % biodegradable materials, including substrates that comprise at least 80 wt. % biodegradable materials and substrates that comprise at least 85 wt. % biodegradable materials.

Substrates made from the nanofibrils are mechanically flexible and optically transparent. For the purposes of this disclosure, a substrate is considered optically transparent if it has a transmittance of at least 55% over the wavelength range from 400 nm to 800 nm. This includes substrates having a transmittance of at least 60%, at least 70% and at least 80% over that wavelength range. Unlike conventional paper, in which the fibers dimensions are typically in micrometer scale, the CNF substrate is comprised of nanoscale fibers having an average fiber diameter in the range from about 5 to about 20 nm (in some embodiments of the CNF substrates all or substantially all—i.e., ≥90% of the fibers—have a diameter in the range from about 5 to 20 nm), and lengths of up to several microns, which makes the entire substrate optically transparent. The CNF substrates also do not contain filler particles that are used to render paper opaque for printing or sizing additives that are used to provide suitable absorbency for printing inks. The CNF substrates also lack light-sensitive materials or coatings that are used in photographic papers. The CNF substrate is coated with an optically transparent encapsulating hydrophobic polymer that increases the hydrophobicity of the substrate, thereby improving its manufacturing capability and mechanical properties. However, some embodiments of the CNF substrates comprise thermally conductive particles dispersed in the cellulose nanofibrils in order to increase the thermal conductivities of the substrates. These particles should have a low dielectric constant, a high thermal conductivity and microwave transparency. Some such particles have a thermal conductivity of at least 30 W/mK, at least 50 W/mK and at least 100 W/mK. Examples of suitable materials for the thermally conductive particles include boron nitride, aluminum nitride particles and diamond particles, which are electrically insulating and highly thermally conductive. Depending on the value of the desired thermal conductivity, the loading contents of these particles may vary and can reach as high as 50 wt. %. For example the substrates may have a particle loading in the range from about 0.1 to about 50 wt. %.

For the purposes of this disclosure, a material is considered biodegradable if the material experiences a weight loss of at least 10% when subjected to a fungal biodegradation test using any decay fungi that are inhabitants of forest ecosystem, including *postia placenta* and/or *phanerochaete chrysosporium*, for 28 days at 27° C. and 70% relative humidity, carried out as described in the Example below.

The CNF substrates are characterized by low RF loss tangents, rendering them suitable for use in microwave devices. For example, some embodiments of the CNF substrates have an RF loss tangent of no greater than 0.045 across the frequency range of 1 to 10 GHz. This includes embodiments of the CNF substrates that have an RF loss tangent of no greater than 0.043 across the frequency range of 1 to 10 GHz. The Example below provides a description of the method for determining the RF loss tangent of a substrate.

The CNF substrates are further characterized by low dielectric constants. For example, some embodiments of the CNF substrates have a dielectric constant of no higher than 3 across the frequency range of 1 to 10 GHz. This includes embodiments of the CNF substrates that have a dielectric constant of no greater than 2.8 across the frequency range of 1 to 10 GHz. The Example below provides a description of the method for determining the dielectric constant of a substrate.

The CNF substrates are thermally stable and suited for operation at high voltages. By way of illustration, some embodiments of the CNF substrates are thermally stable at operating temperatures of 200° C., or higher, and do undergo electric breakdown even at voltages of 1000 V, or higher.

The Example below provides a description of the methods for determining the thermal stability and the breakdown voltage of a substrate.

It should be noted that the CNF substrates of the microwave integrated circuits serve as primary substrates that support critical functions of the circuits, including heat dissipation and signal distribution, and are in direct contact with one or more active components of the circuitry. They may also be in direct contact with one or more passive components of the circuitry. (A component that is coated in a substantially water insoluble polymer, as described previously, is considered to be in direct contact with a CNF substrate even if it is the coating that makes the contact. Similarly, if an adhesive coating is used to adhere a component of the integrated circuitry to the CNF substrate, that component is still considered to be in direct contact with the CNF substrate. Adhesive coatings that can be used for this purpose include, but are not limited to, polyimide-based adhesives, such as SU-8. However, other adhesive thermoset resins could also be used.) As such, the CNF substrates are part of the integrated circuit and can be distinguished from secondary substrates onto which fully formed and self-contained active and passive components and/or integrated circuit (for example, commercially available Schottky diodes, bipolar transistors or full microwave chips) are placed only after they been fabricated on another, non-biodegradable, dielectric substrate (e.g., ceramic, glass or semi-insulating GaAs). Thus, in the present microwave integrated circuits the active and/or passive components do not include a non-biodegradable dielectric substrate in addition to the dielectric CNF substrate. Even if the active and/or passive components are fabricated on a non-biodegradable substrate, that substrate is removed prior to the transferring the active and/or passive components onto the CNF substrate. By way of illustration only, in the present microwave integrated circuits, the subcollector of a GaAs-based heterojunction bipolar transistor can be in direct contact with the CNF substrate—without an intervening layer of semi-insulating GaAs substrate.

Because the present microwave integrated circuits omit the non-biodegradable substrates of conventional microwave integrated circuits, they can provide microwave integrated circuits that are substantially biodegradable. For the purposes of this disclosure, an integrated circuit is considered "substantially biodegradable" if it comprises at least 80 weight percent (wt. %) biodegradable materials. This includes embodiments of the integrated circuits that comprise at least 75 wt. % biodegradable materials. This is particularly advantageous for microwave circuits that comprise toxic materials, such as arsenic, because it can reduce the concentration of those materials to very low levels, making it possible to dispose of the devices without harming the environment.

As illustrated in detail in the Example below, the substantially biodegradable microwave integrated circuits can be made by forming passive and active components for a microwave integrated circuit on one or more non-biodegradable substrates, wherein at least one of the active components comprises a Group III-V semiconductor. The passive and active components are then released from the substrate(s) upon which they were formed and transferred onto the CNF substrate. Optionally, an adhesive applied to the CNF substrate, the components, or both, may be used to facilitate the transfer. In this manner any non-biodegradable support substrates used in the fabrication of the passive and active components can be removed prior to the transfer of the circuitry onto the CNF substrate, thereby substantially reducing the non-biodegradable material content of the microwave integrated circuits. An advantage of this "release and transfer" approach to building the integrated circuits is that the non-biodegradable substrate upon which the active and/or passive components are initially formed can be re-used after each transfer.

EXAMPLE

This example illustrates the microwave applications of CNF and demonstrates high performance electronics that are comparable to existing state-of-the-art electronics, including process-complicated GaAs-based microwave level electronics where the operating frequency is beyond gigahertz, as well as Si-based digital electronics, on CNF substrates. Fungal biodegradation of these CNF-based electronics, for the purpose of cycling degraded CNF back to forestry as fertilizer, was also carried out to show the decaying process over time. While transfer printing techniques and CNF substrate are used to realize various high-performance flexible electronics in this work, what is described is a new, much more sustainable, green electronic chip concept to address the societal impact of today's economically important yet environmentally unsustainable consumer electronics, based on the important and newly discovered RF properties of CNF substrates.

Results

Cellulose Nanofibril Film and its Characteristics

Figure 2:
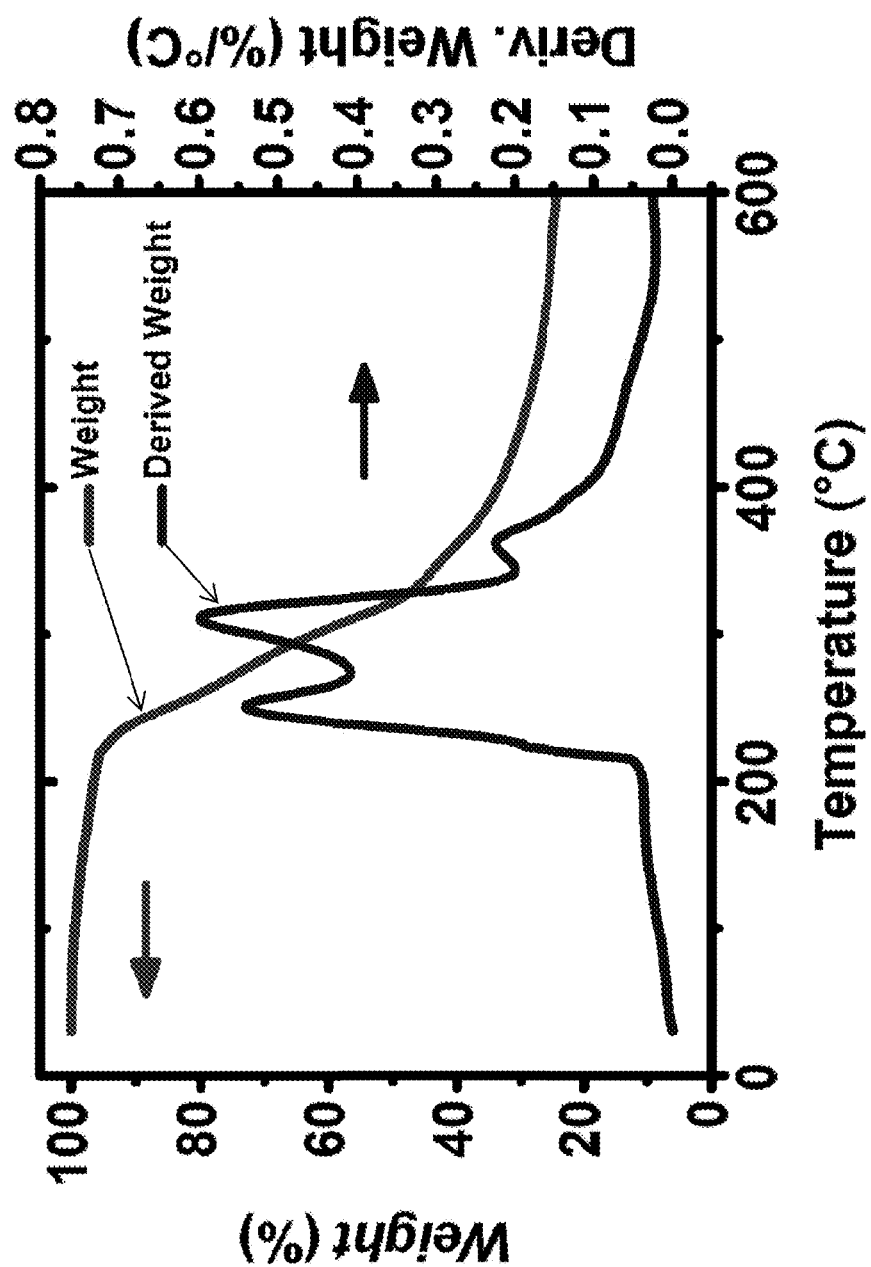
FIG. 2. A thermogravimetric (TGA) plot showing the weight change of the CNF film as a function of temperature, along with the first derivative of the curve. The film remains stable up to 213° C.
Figure 3:
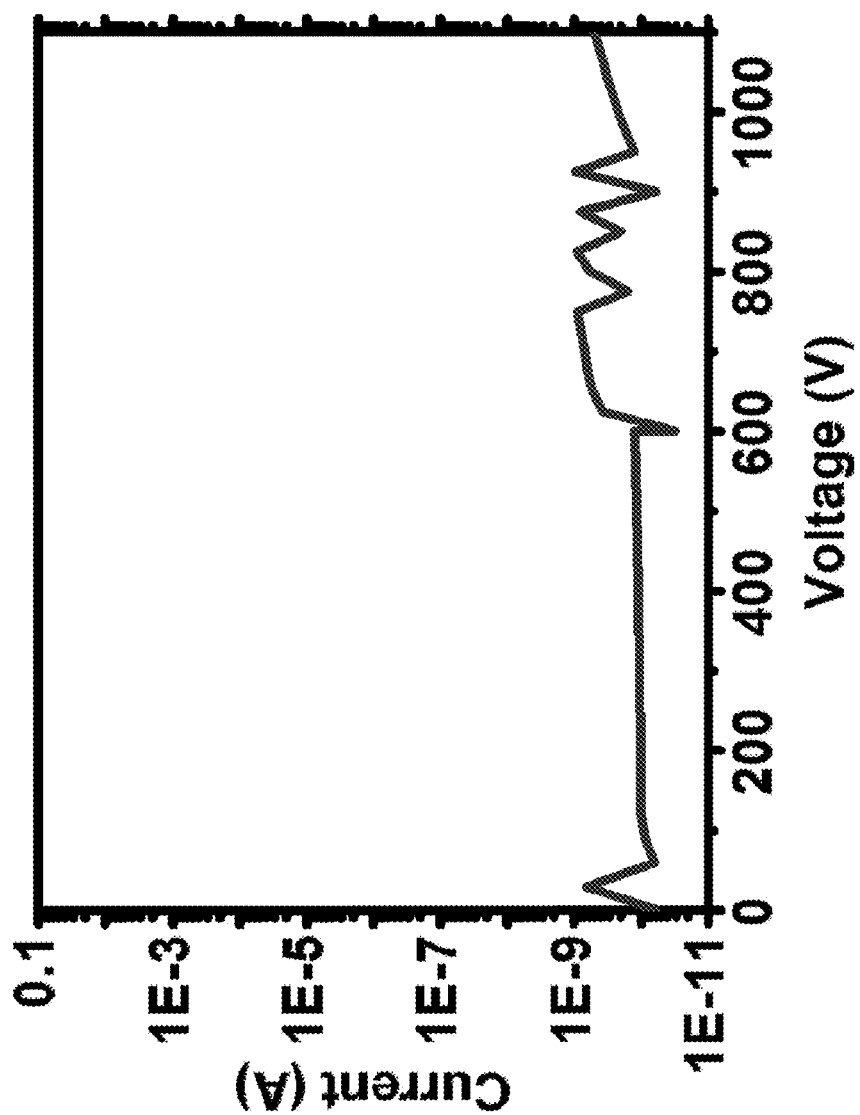
FIG. 3. The electrical breakdown characteristics of the CNF film. Current is measured while high voltage is applied on both sides of the film.
Figure 4:
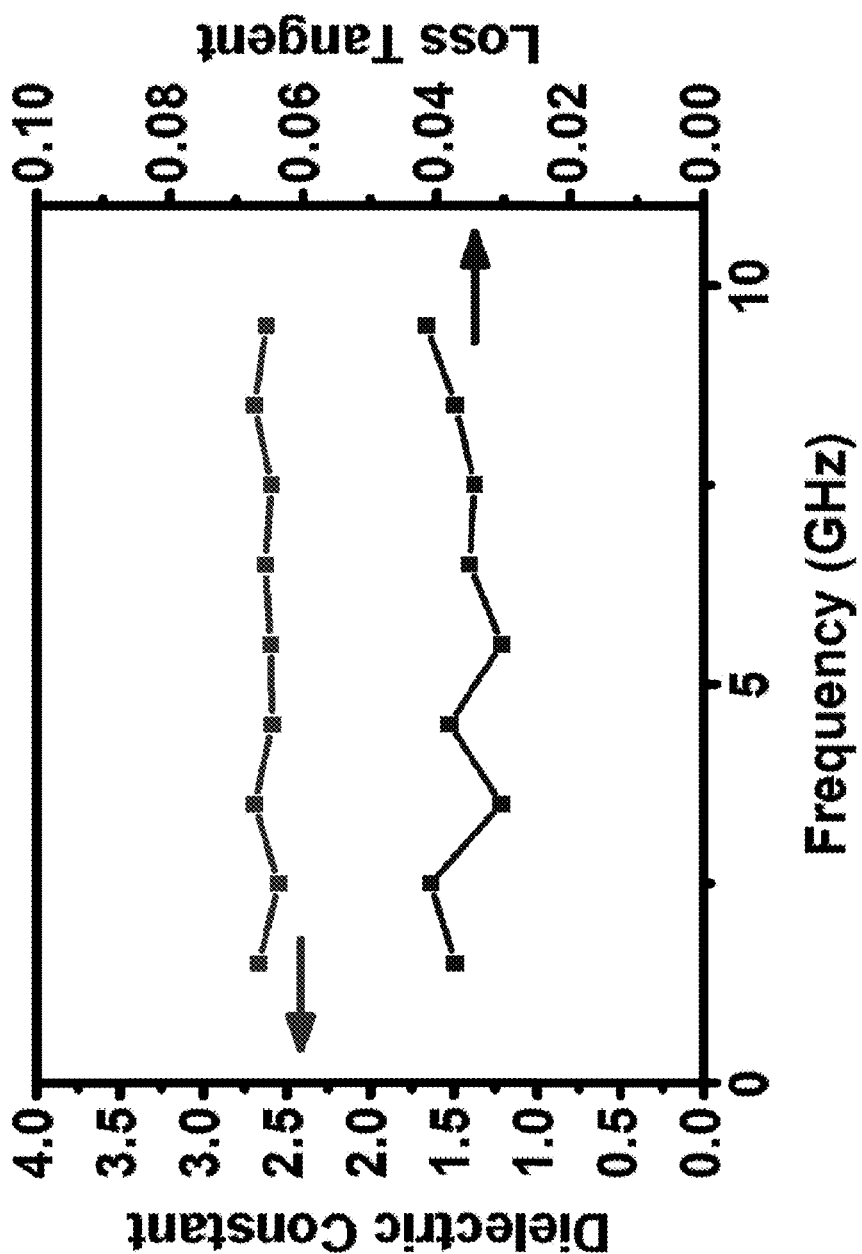
FIG. 4. Radio frequency characteristics of the CNF film. Dielectric constant (upper curve) and loss tangent (lower curve) are measured in the frequency range of 0 to 10 GHz using a microstrip waveguide.

In the life cycle of the CNF substrates the CNF film is first made from CNFs extracted from the woods, degraded via a fungal biodegradation process upon disposal, and then can be sent back to the woods without adverse environmental effects. Electronic systems based on such material could significantly facilitate recycling and management of waste streams. Thus, the ecofriendly wood-based CNF substrate is an ideal substitution for other electronics substrates that exist today. However, pure CNF film is vulnerable to water. To address this issue, the pure CNF film was coated with a bisphenol A-based epoxy resin. The epoxy coating increased the contact angle of the CNF film from 28.4° to 74.6°, thereby making the CNF film much more hydrophobic. This treatment allowed for easier handling of the CNF substrate and offered better manufacturing capabilities. Epoxy is a type of thermoset plastic commonly used in electronics packaging materials (e.g., electronic molding compounds as well as underfills) due to its ease of handling, desirable materials properties, and relatively low cost. The epoxy coating can also enhance the mechanical properties of the CNF film. FIGS. 1-4 introduce the unique material properties of the epoxy-coated CNF films. As shown in FIG. 1, the CNF film was transparent, thus making it ideal for certain applications. The transmittance was over 80% for an 80 μm thick CNF film and 60% for a 220 μm thick CNF film over the visible spectrum. FIG. 2 presents thermogravimetric analysis (TGA) data showing the weight loss of the epoxy-coated CNF film as a function of temperature as well as the first derivative of the TGA curve. There were three peaks in the differential TGA curve, with the first (213° C.) and third (270° C.) peak corresponding to the decomposition of the CNF and epoxy process, respectively. The middle peak observed at 310° C. was attributed to the overlapping of the CNF and epoxy decomposition peaks. The glass transition temperature ($T_g$) of the film was measured at 72.8° C., which was similar to that of polyethylene terephthalate (PET) film, a commonly used substrate for flexible electronics. In addition, the CNF film was strong and flexible enough to allow reversible bending. The flexural modulus of the epoxy-coated CNF film was calculated to be 2.5 GPa, which is comparable to that of PET (1.5 to 2.8 GPa). The electrical properties of the CNF film were also appealing for use with electronics. As presented in FIG. 3, the CNF film did not undergo an electrical breakdown, even at very high voltages (e.g., 1100 V), which is far beyond the requirement for consumer electronics. Furthermore, because the dielectric and RF properties of the substrate are major aspects to be considered in designing a RF circuit, the RF loss and dielectric constant were extracted using a microstrip waveguide and analyzed at high frequencies. In the frequency range from 0 to 10 GHz, the dielectric constant ranged from 2.58 to 2.69, and the loss tangent ranged from 0.0302 to 0.0415, as presented in FIG. 4. The above characterizations for the first time unveiled the suitability of the CNF substrates for high-frequency microwave applications. While the dielectric constant and RF loss values were comparable to those of PET film, the biodegradability property of CNF makes it a superior candidate over PET for addressing the abovementioned environmental impact.

Fabrication Process of GaAs Devices on CNF Substrates

Figure 5:
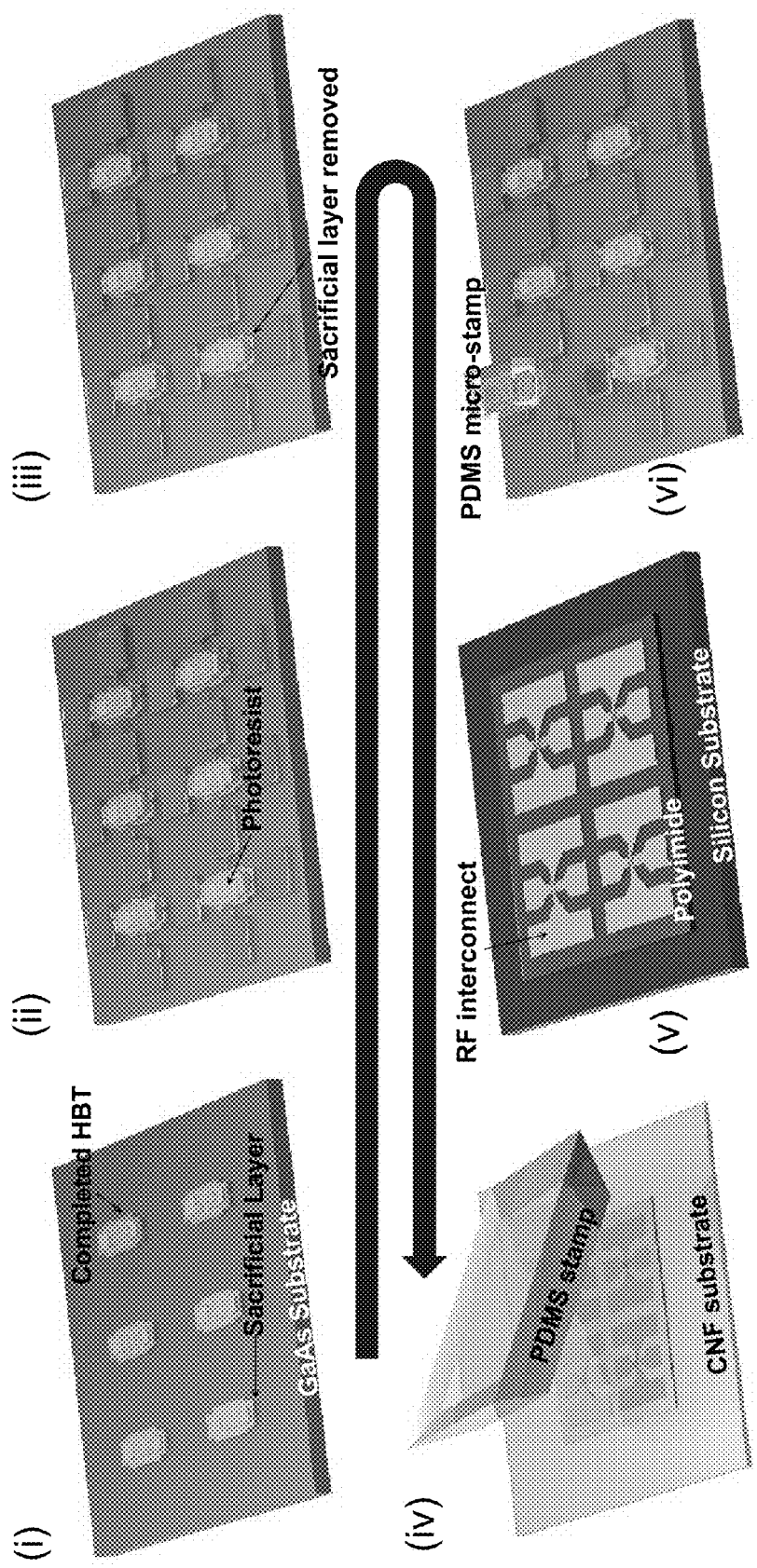
FIG. 5. Schematic illustration of the fabrication process of GaInP/GaAs HBTs on a CNF substrate.
Figure 7:
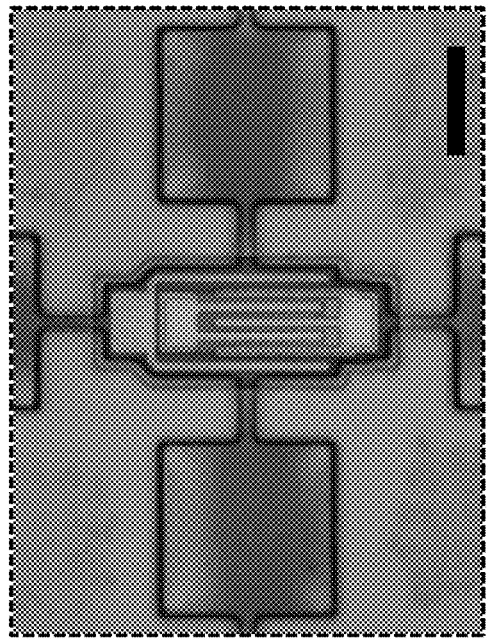
FIG. 7. An optical image showing a single releasable HBT that is tethered to the substrate with photoresist anchors. Scale bar, 30 μm.
Figure 6:
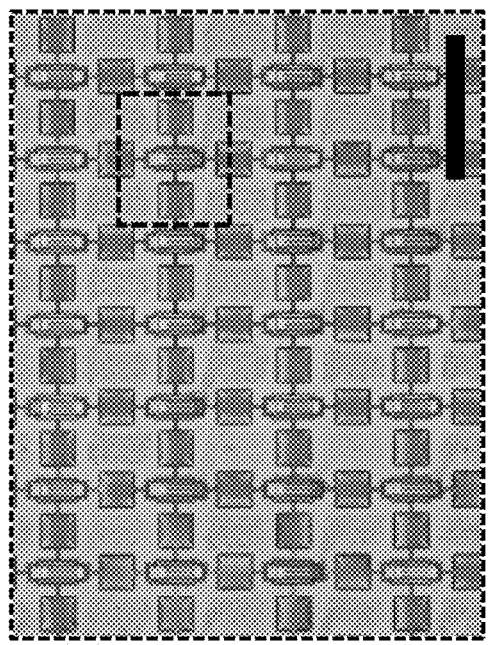
FIG. 6. A magnified image of an array of 1,500 HBTs on a GaAs substrate. Scale bar, 200 μm.

Compared to devices operating at low frequencies (~MHz) or direct current (DC) levels, microwave (~GHz) devices are especially difficult to fabricate on foreign substrates, due to the small feature sizes and high temperature processes required for high performance. Here, for the first time, methods to fabricate microwave GaAs-based devices on foreign substrates, namely the CNF substrate are presented. It should be noted that the majority of today's portable gadgets (>85% in cell phones) with wireless communication functions employ GaAs-based microwave devices for their superior high-frequency operation and power handling capabilities. FIG. 5 outlines the procedure for manufacturing GaInP/GaAs heterojunction bipolar transistors (HBTs) on a CNF substrate via schematic illustrations. Thin heterojunction epitaxial layers in stacks of n-cap layer (GaAs:Si)/n-emitter layer (GaInP:Si)/p-base layer (GaAs:C)/n-collector layer (GaAs:Si)/n-sub-collector layer (GaAs:Si) were grown on a 500 nm thick sacrificial layer ($Al_{0.96}Ga_{0.04}As$) on a GaAs wafer. The fabrication process began by following conventional procedures to fabricate the HBTs (FIG. 5, panel(i)), followed by protective anchor patterning using a photoresist (PR) (FIG. 5, panel(ii)). This will protect the devices and allow the devices to be tethered to the substrate after etching away the underlying sacrificial layer using a diluted hydrofluoric acid (HF) solution (FIG. 5, panel(iii)). Van der Waals contact with a soft elastomer stamp made of polydimethylsiloxane (PDMS) to the device breaks the anchors on all four sides and easily picks up a single device (FIG. 5, panel(iv)). The devices are transfer printed in deterministic assembly onto a temporary Si substrate using ultrathin polyimide (PI, ~1 μm) as an adhesive, followed by ground-signal-ground (G-S-G) RF interconnect metallization (FIG. 5, panel(v)). Polyimide is an excellent material for GaAs-based devices not only as an adhesive, but also as a passivating material that can suppress the high surface states of GaAs and prevent leakage current. Devices are then released from the temporary substrate and printed onto a CNF substrate using a PDMS stamp ((FIG. 5, panel(vi))). FIGS. 6 and 7 present optical microscopy images of fully formed HBTs on a GaAs substrate that are ready to be picked up. An array of 1,500 releasable HBTs on a 5×6 $mm^2$ GaAs substrate was fabricated. FIG. 6 is a magnified image of a portion of the array. FIG. 7 shows a single releasable HBT tethered to the substrate with photoresist anchors. The array of HBTs on a CNF substrate were flexible enough to be wrapped around a tree stick, demonstrating the high flexibility of these electronics.

Analysis of the Influence of GaAs on the Environment

Figure 8:
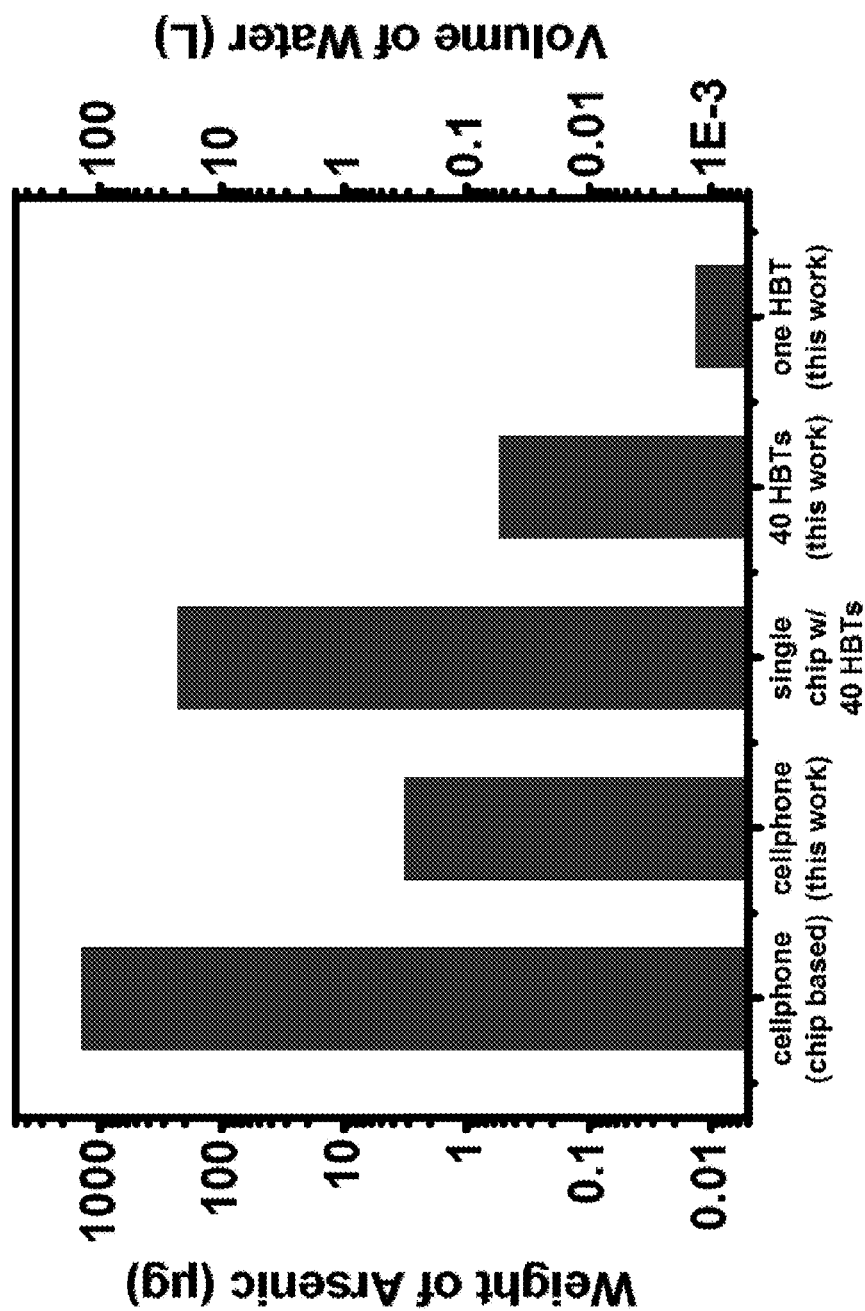
FIG. 8. Comparison chart showing the amount of the arsenic corresponding to each type of device/transistor listed, as well as the amount of water calculated according to the EPA standard based on the quantity of the arsenic present in these devices/transistors.

The Environmental Protection Agency (EPA) has set the Arsenic standard for drinking water at 10 parts-per-billion (ppb), i.e., 10 μg L$^{-1}$. Compared to a typical GaAs MMIC, which only consists of a few HBTs on a large substrate, this pick-and-place method greatly reduces the usage of expensive and hazardous semiconductor materials. FIG. 8 presents a quantitative analysis of the amount of arsenic present in the corresponding device/transistor due to the usage of GaAs that may lead to adverse environmental impact. Also shown in FIG. 8 is the amount of water calculated according to the EPA standard based on the amount of arsenic present in these devices/transistors. This analysis shows that a significant amount of clean water can be saved or preserved using this deterministic assembly approach in making the GaAs-based electronics. The weight of arsenic was obtained by converting the measured volume of either conventional GaAs chip or the printed HBTs to weight. As an example, a conventional miniature GaAs HBT based MMIC with 40 HBTs on a 1.15×0.75 mm$^2$ large and 100 μm thick substrate, was used as a reference for the comparison. (See, Kawamura, H. et al. A miniature 44% efficiency GaAs HBT power amplifier MMIC for the W-CDMA application. *GaAs IC Symposium,* 2000. 22$^{nd}$ Annual Seattle, Wash., November 5-8, pp 25-28 (2000).) Moreover, a single GaAs HBT with a CNF substrate with a volume of 5.04×10$^{-6}$ mm$^3$ was used. Assuming that there are six GaAs HBT-based MMIC chips in a typical cell phone, approximately 138 L of water is required at minimum to meet the standards, whereas, the same cell phone using the present approach only requires 0.32 L of water. For a single conventional chip with 40 HBTs, 22.9 L of water is required, whereas only 0.054 L is required for the 40 HBTs fabricated using the present method. This approach is even more advantageous where only a few HBTs are required. For instance, a single conventional chip with 40 HBTs and 20 HBTs would have similar weight because they are typically built on a similarly sized substrate; however, 20 HBTs printed using the present approach would weigh exactly half of the 40 HBTs. In fact, a single printed HBT only requires 0.0013 L of water to meet the EPA standard for drinking water.

Microwave GaAs Electronic Devices on CNF Substrates

Figure 9:
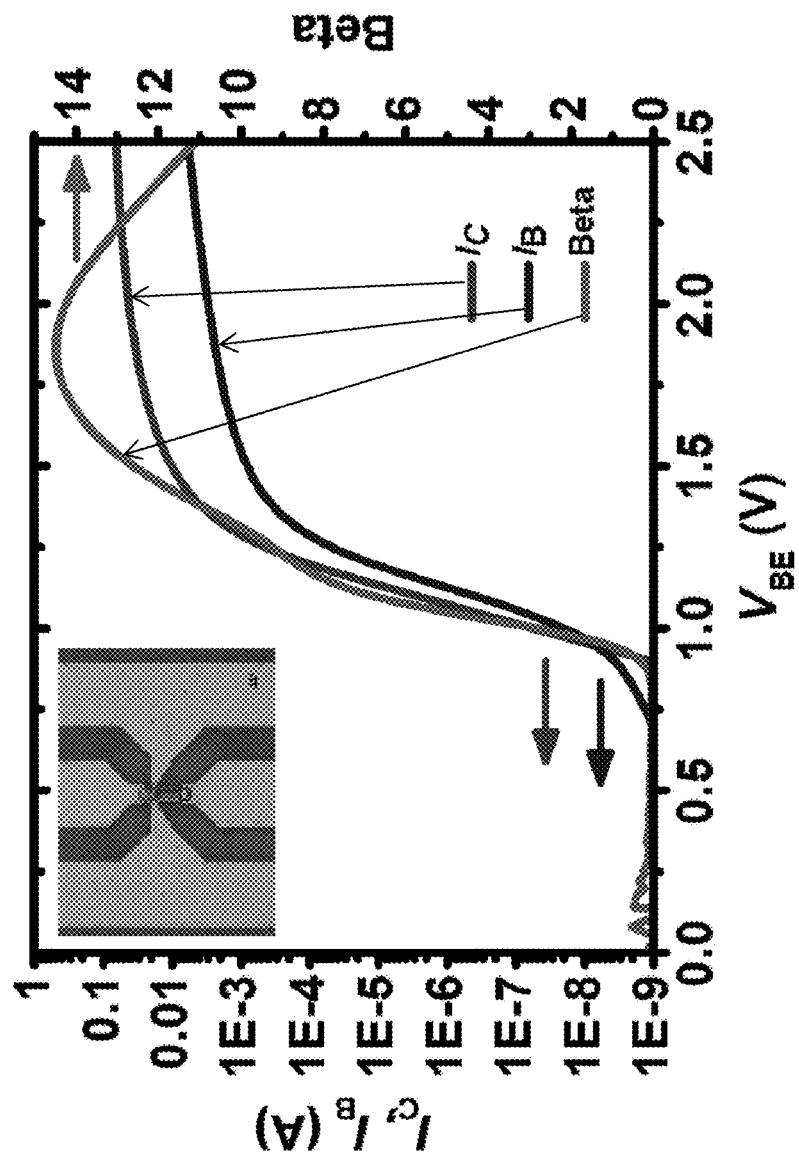
FIG. 9. Gummel plot and Beta plot showing the maximum DC gain of an HBT on a CNF substrate. The maximum beta is 14.49. The inset optical image shows one of the HBTs in the array that was measured and characterized.
Figure 10:
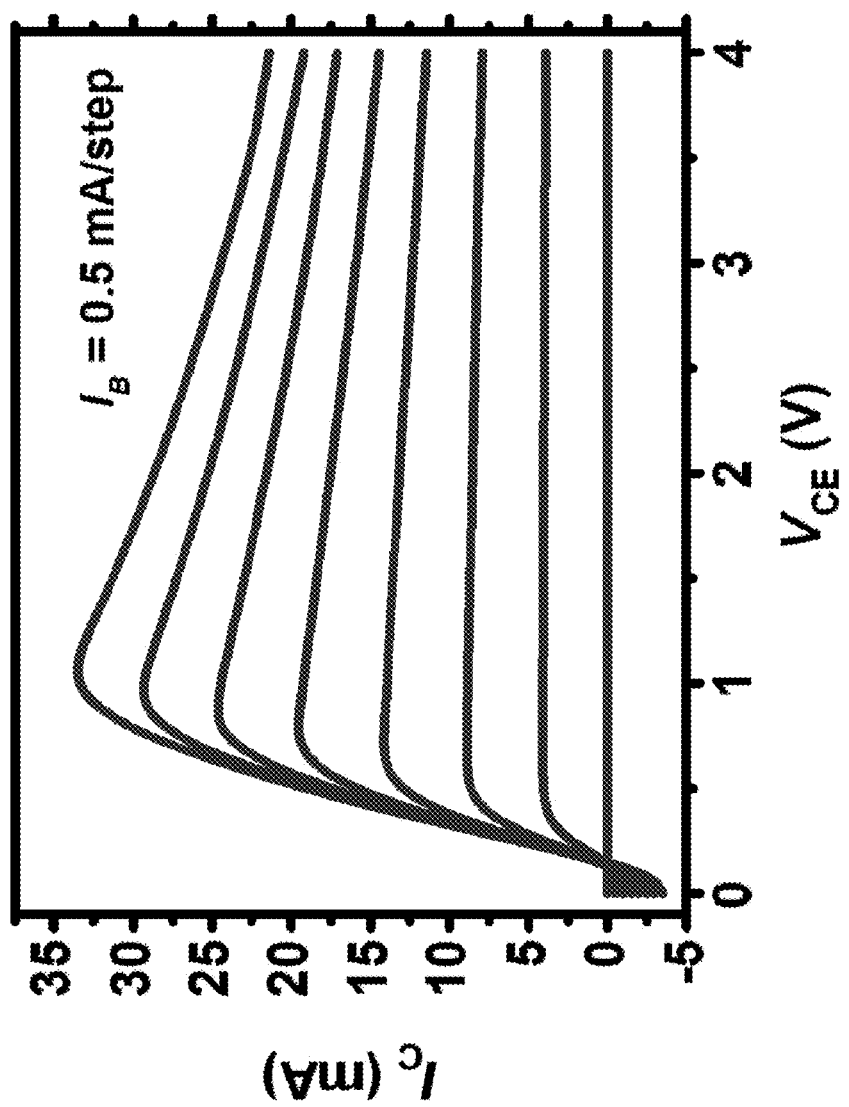
FIG. 10. $I_C$ vs. $V_{CE}$ plot of the HBT plotted at 0.5 mA steps of $I_B$.
Figure 11:
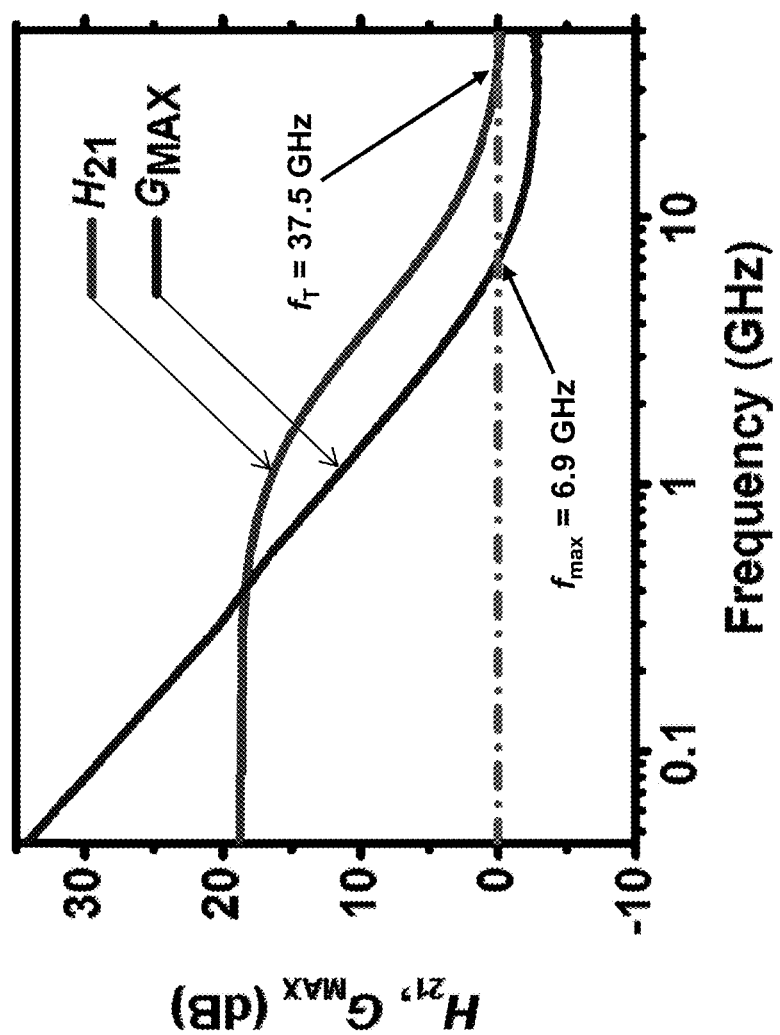
FIG. 11. Current gain ($H_{21}$) and power gain ($G_{MAX}$) of the HBT as a function of frequency, with a collector voltage bias of 2 V and a base current bias of 2 mA.

FIGS. 9-11 show the electrical properties of a single finger (2×20 μm$^2$) non-self-aligned HBT on a CNF substrate. The Gummel plot presented in FIG. 9 reflects collector and base electric current, $I_C$ and $I_B$, against base-emitter voltage, $V_{BE}$ with zero $V_{BC}$ bias. The common-emitter current gain curve under zero $V_{BC}$ bias is shown in highest curve in FIG. 9, which indicates that the beta (β) had its maximum value of 14.49 at a $V_{BE}$ of 1.86 V. Under an extreme bending condition (i.e., at a bending radius of 2.5 mm), the maximum beta value decreased slightly to 13.64. The $I_C$ vs. $V_{CE}$ curve is presented in FIG. 10. The positive $V_{CEOFFSET}$ value of 0.14 V is due to the single heterojunction structure of the HBT where the offset comes from the difference in bandgap between the emitter (GaInP) and the base (GaAs). The decaying collector current observed as $V_{CE}$ was increased at high base current is attributed to poor thermal dissipation as the thermal conductivity of the underlying CNF substrate (κ=1.0 W m$^{-1}$ K$^{-1}$) was lower than that of a typical GaAs substrate (κ=56 W m$^{-1}$ K$^{-1}$). The RF performances of the HBT were analyzed from the measured scattering (S—) parameters from 0.045 to 50 GHz. Open and short patterns of the probing pads on the CNF substrate were used to subtract the effect of parasitic inductances and capacitances of the pad. FIG. 11 presents the current gain ($H_{21}$) and power gain ($G_{MAX}$) against frequency for the device under a bias of $V_C$=2 V and $I_B$=2 mA. A high cut-off frequency ($f_T$) of 37.5 GHz and a maximum oscillation frequency ($f_{max}$) of 6.9 GHz were obtained. The relatively low $f_{max}$ of 6.9 GHz was attributed to the non-self-aligned structure of the HBT where large emitter-base spacing (2 μm) introduced high base resistance, causing the $f_{max}$ to drop. These outstanding RF results further prove the suitability of CNF for microwave applications. Although a decay of current at increasing voltages due to the relatively low thermal conductivity of the CNF film was observed, the frequency responses of the HBT were sufficiently high to be used as practical amplifiers in mobile devices where the cellular frequency is in the range of 800 to 2500 MHz. By incorporating materials with high thermal conductivities, such as boron nitride or diamond nanoparticles into the CNF film, the device performance can be further improved.

Figure 12:
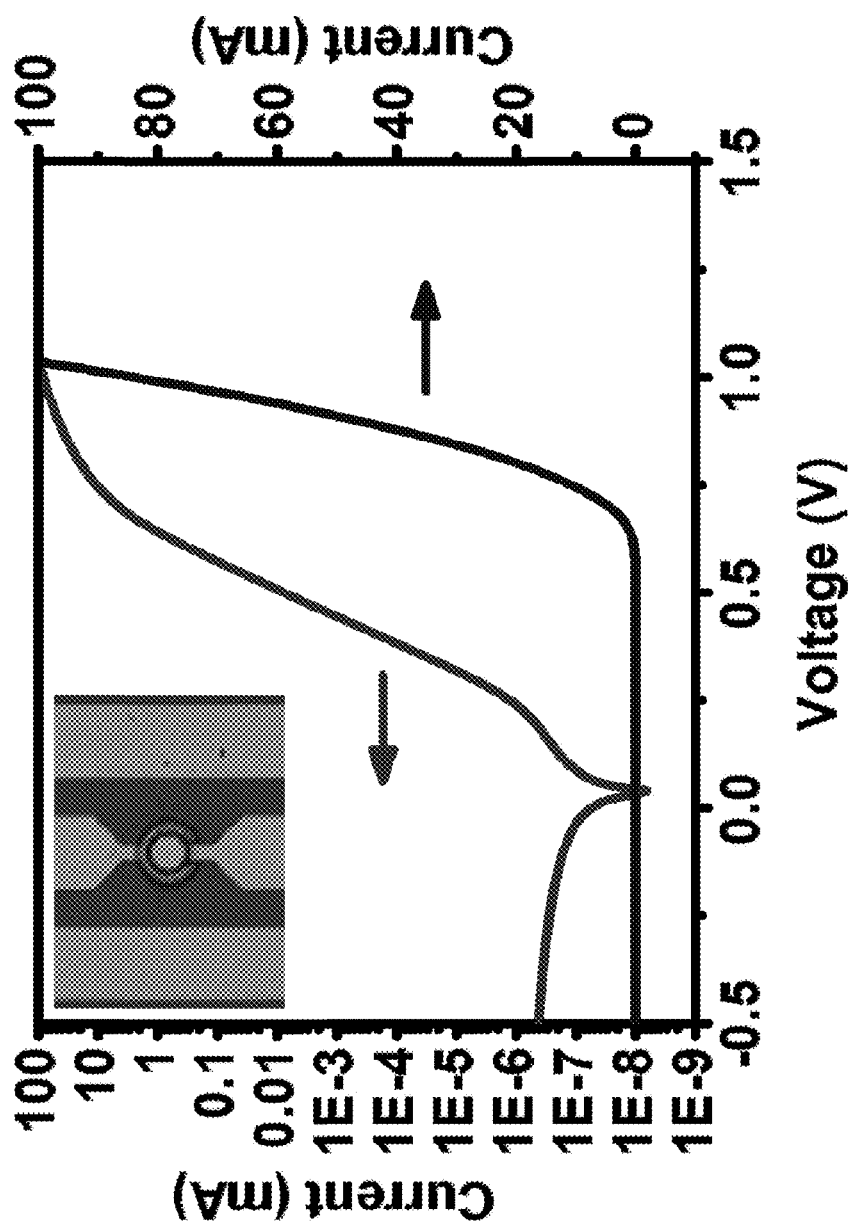
FIG. 12. Current versus voltage plot of a Schottky diode on a CNF substrate. The left-most curve shows the logarithmic scale and the right-most curve shows the linear scale. The inset optical image shows the diode transferred onto a CNF substrate with G-S-G interconnects.
Figure 13:
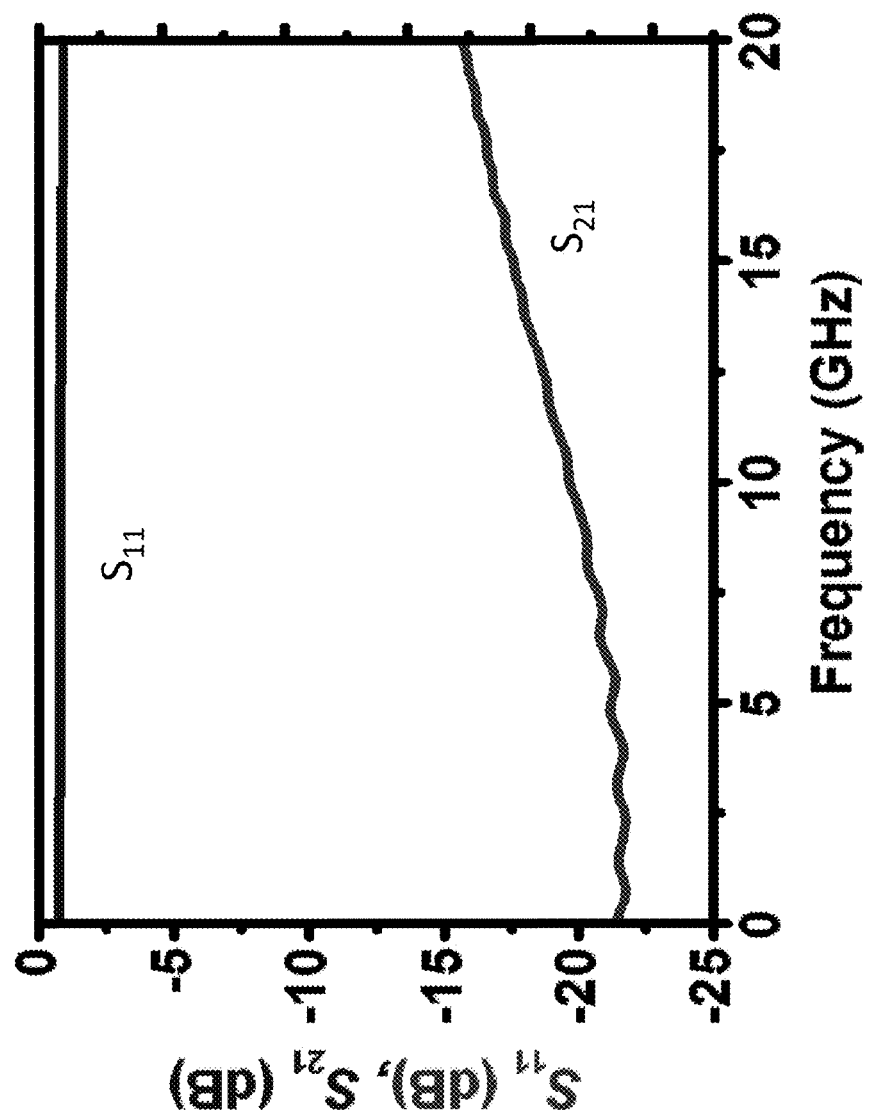
FIG. 13. Measured $S_{11}$ (lower) and $S_{21}$ (upper) plotted against frequency under a forward current bias of 10 mA.
Figure 14:
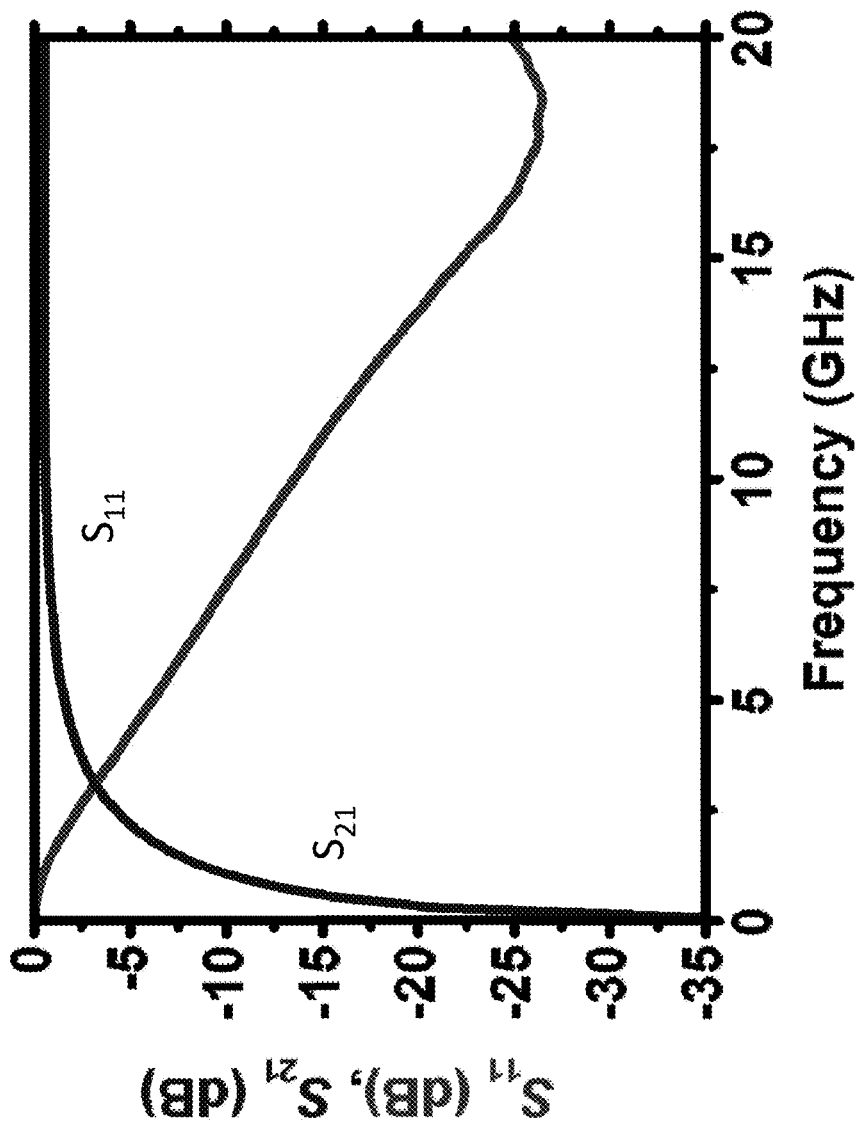
FIG. 14. Measured $S_{11}$ (descending) and $S_{21}$ (ascending) plotted against frequency under a reverse voltage bias of −0.5 V.

Schottky diodes based on GaAs are commonly used in high speed communication systems as mixers and rectifiers. The same fabrication techniques shown in FIG. 5, with minor changes, can be implemented to fabricate high performance Schottky diodes. Similar to the HBTs, nearly 1,200 Schottky diodes with high yield were fabricated on a 5×6 mm$^2$ GaAs substrate. FIG. 12 (with an inset image showing the measured diode) presents the DC performance of the diode measured on a CNF substrate, where an ideal Schottky behavior with a low turn on voltage of 0.7 V was obtained. A logarithmic plot (left curve) of the data shows a good ideality factor of 1.058. FIGS. 13 and 14 present the measured S-parameters of the diode at forward bias and reverse bias, respectively. At a forward current bias of 10 mA (V=740.6 mV), the insertion loss ($S_{21}$) was only −1 dB at 20 GHz, making it suitable for RF applications. At a reverse voltage bias of −0.5 V (I=−414.1 pA), the insertion loss ($S_{21}$) reached −2 dB at 4.3 GHz. The low resistance obtained under reverse bias at high frequencies shows that these diodes can perform with high switching speeds in microwave circuits.

Figure 15:
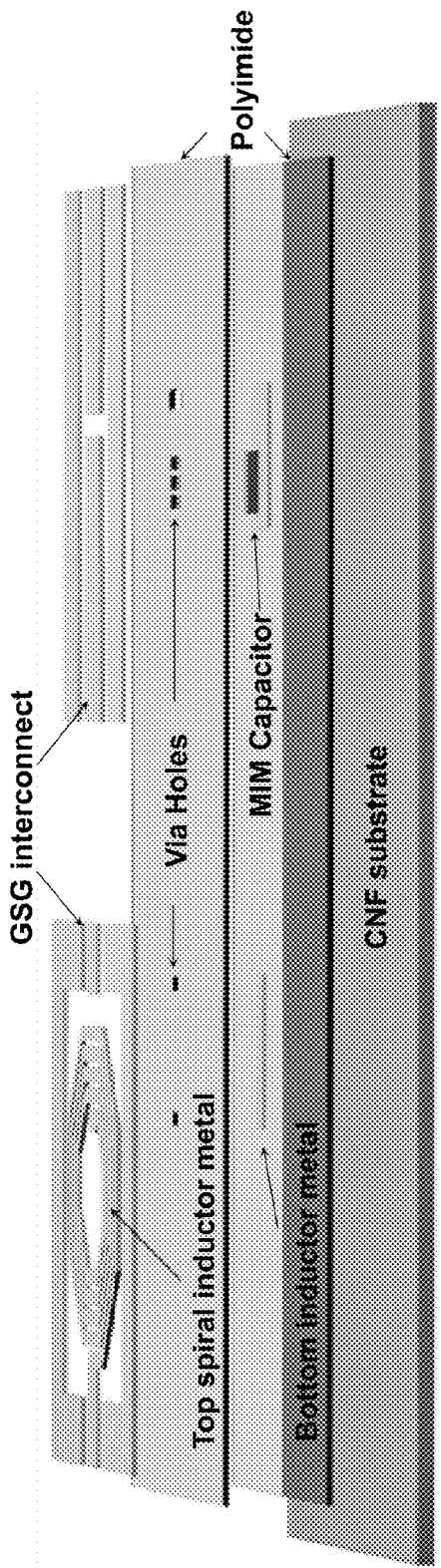
FIG. 15. An exploded view schematic illustration of an inductor and capacitor on a CNF substrate.
Figures 16, 17, 18:
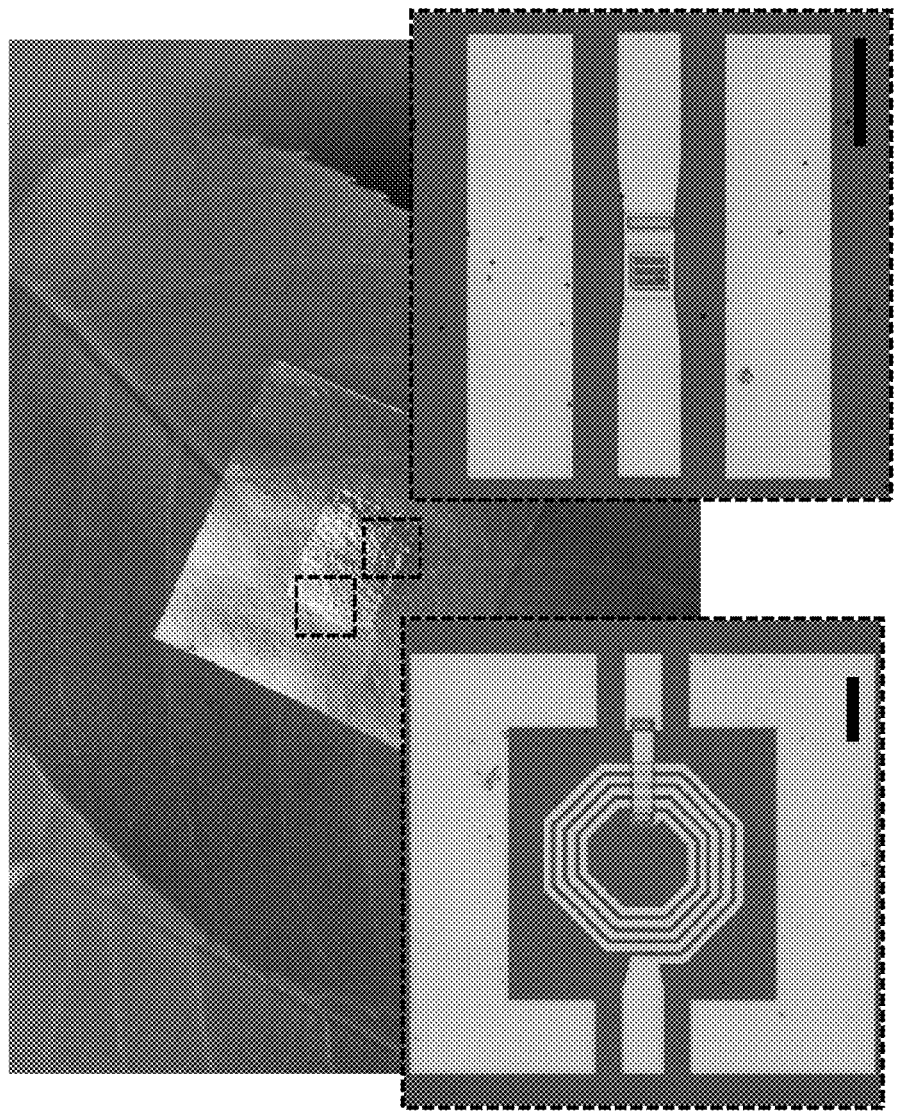
FIG. 16. Array of inductors and capacitors on a CNF substrate put on a tree leaf.
FIG. 17. Optical image of the measured 4.5 turn inductor. Scale bar, 100 μm.
FIG. 18. Optical image of the measured MIM capacitor. Scale bar, 100 μm.
Figure 19:
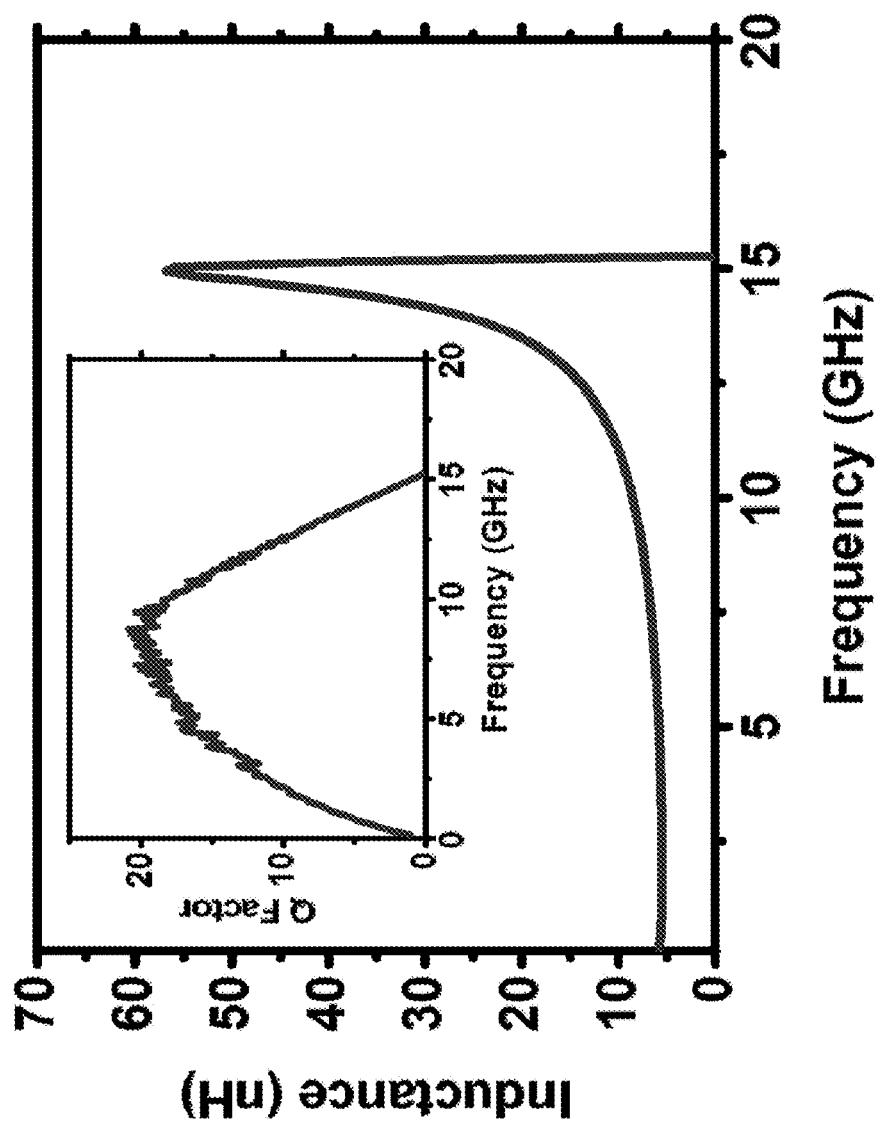
FIG. 19. Inductance plotted against frequency with an inset plot showing the inductor Q factor as a function of frequency.
Figure 20:
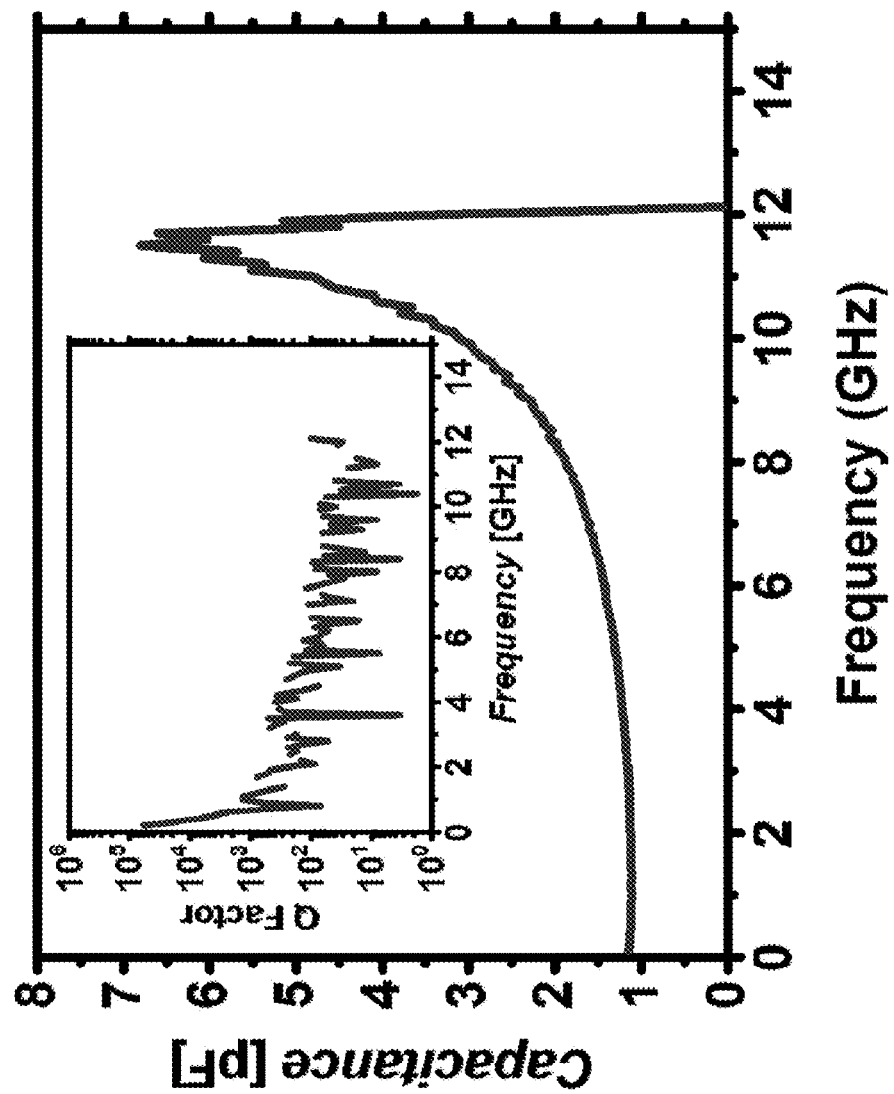
FIG. 20. Capacitance plotted against frequency with an inset plot showing the capacitor Q factor as a function of frequency.
Figure 21:
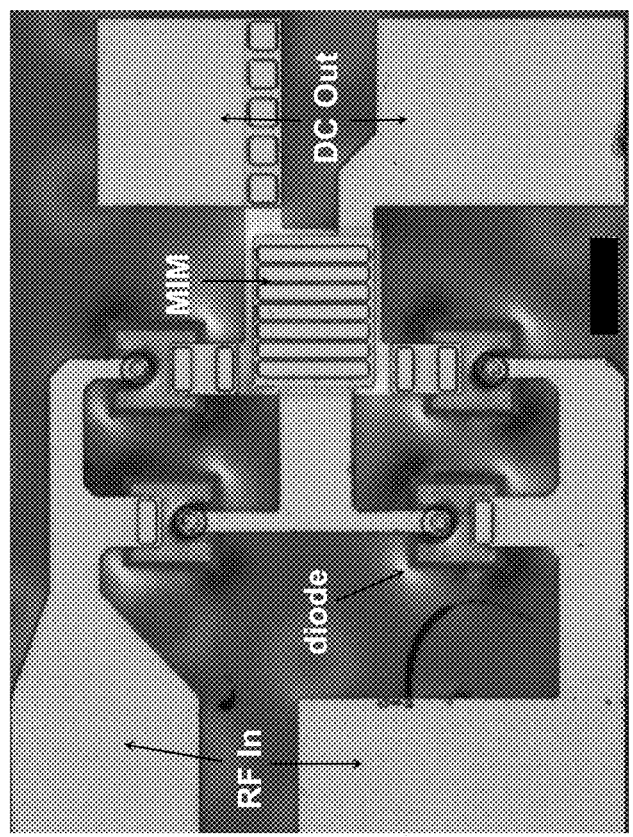
FIG. 21. An optical microscopy image of a full bridge rectifier built on a CNF substrate. Here, the microwave Schottky diodes and an MIM capacitor were integrated. Scale bar, 50 μm.
Figure 22:
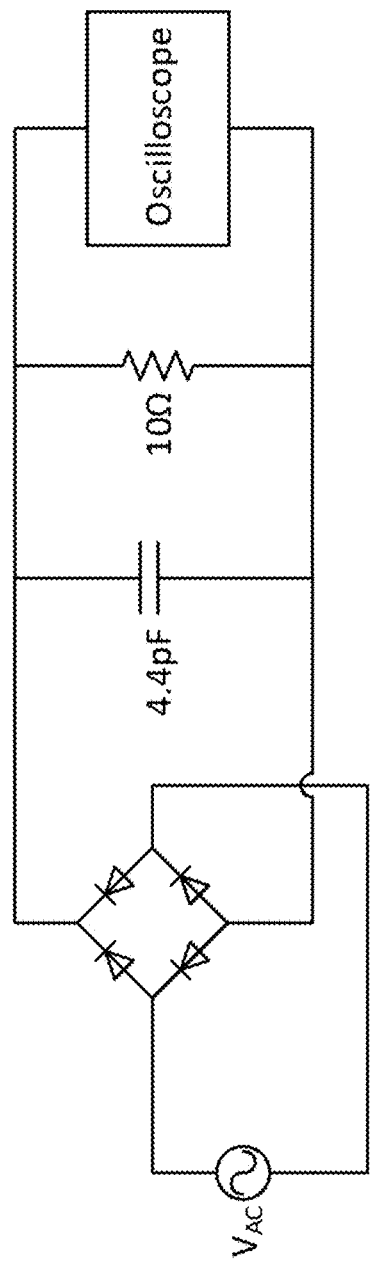
FIG. 22. Circuit diagram of the rectifier built on a CNF film.
Figure 23:
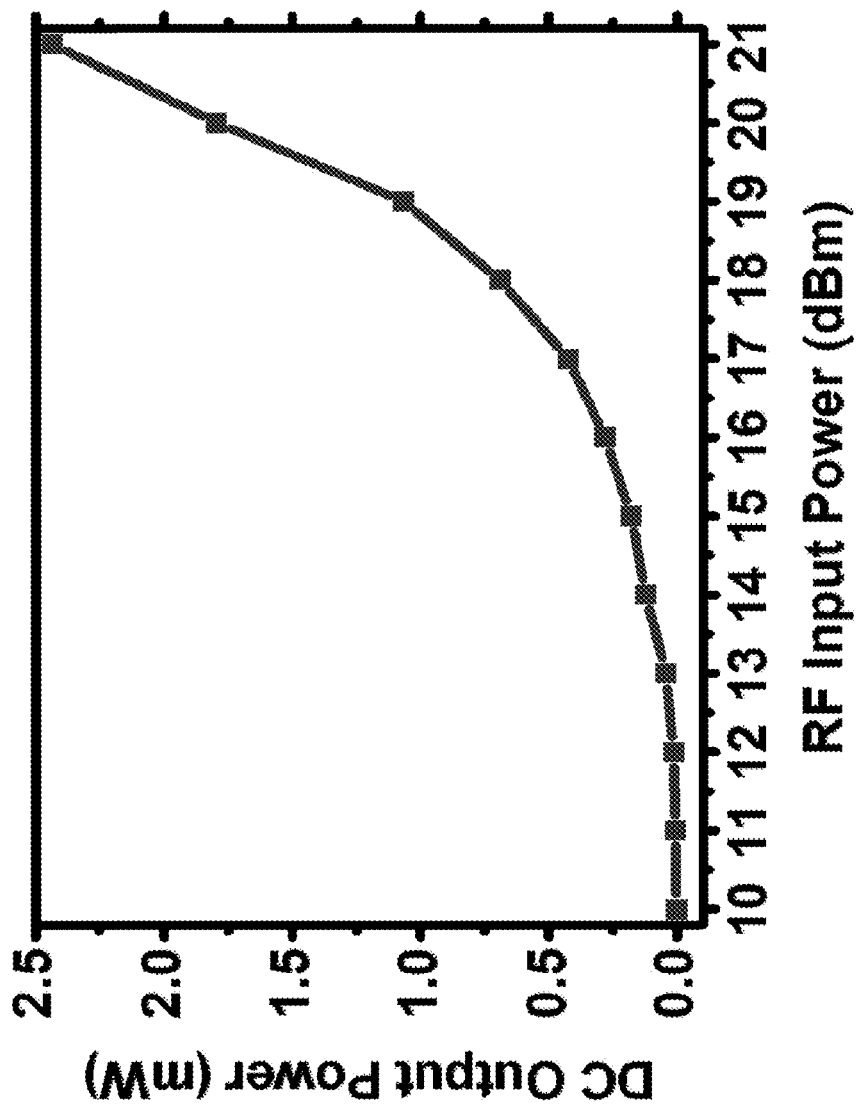
FIG. 23. Measured rectified DC output power of the rectifier while applying RF input power from 10 dBm to 21 dBm at 5.8 GHz.

Passive elements are crucial components that are used for various purposes, such as RF chokes and impedance matching networks in RF circuits. To demonstrate the full capability of the CNF substrate for microwave circuit application, simple metal-insulator-metal (MIM) capacitors and spiral inductors were fabricated on a CNF substrate. FIG. 15 presents the structure of the two passive elements on a CNF substrate with schematic illustrations. Bottom inductor metal and MIM capacitors, with 200 nm of $TiO_2$ as the dielectric material, were deposited on a releasable thin polyimide (PI, ~1 μm) sheet spin casted on a temporary Si substrate. Another polyimide layer served as via holes during the subsequent metallization step for the G-S-G RF interconnects. The finished passive components were then released from the temporary substrate and transfer printed onto the CNF substrate. FIG. 16 shows an image of the inductors and capacitors on a CNF substrate placed on a tree leaf. FIGS. 17 and 18 show the optical microscopy images of the measured inductor and capacitor, respectively. The inductance of the 4.5 turn inductor versus frequency is plotted in FIG. 19. The width of the metal line of this inductor was 10 μm and the spacing between the adjacent metal lines was 5 μm. A constant inductance of ~6 nH was obtained up to ~8 GHz, with a self-resonant frequency ($f_{res}$) of 15.1 GHz. A peak Q value of ~20 was obtained at 8 GHz as shown in the inset image of FIG. 19. FIG. 20 plots capacitance against frequency for a 30×30 μm$^2$ MIM capacitor with Q factor plotted in the inset image. A constant capacitance of ~1.3 pF was measured up to 6 GHz, with a $f_{res}$ of 12.1 GHz. Such high Q and $f_{res}$ values obtained at a broad frequency range suggest that these inductors and capacitors are applicable for high speed RF integrated circuits, in conjunction with the microwave devices, on CNF substrates. To evaluate the printed microwave devices on a CNF substrate in an application, four microwave GaAs-based Schottky diodes and an MIM capacitor were combined into a simple integrated circuit to form a full bridge rectifier, as optically shown in FIG. 21 with its circuit diagram shown in FIG. 22. The rectification behavior of RF-to-DC conversion at 5.8 GHz is shown in FIG. 23. This frequency is one of the popular frequencies in wireless local area network (WLAN), commonly used in high speed Wi-Fi systems. As shown in the plot, the rectifier can rectify a 21 dBm input signal to an output power of 2.43 mW. The ability to rectify such high frequency signals can be attributed to the excellent electron mobility of GaAs and the low turn-on voltage of the Schottky diodes. With an appropriate matching network, the rectification ratio is expected to increase drastically by enhancing the reflection loss of the circuit.

Silicon-Based Digital Electronics on CNF Substrates

Figure 24:
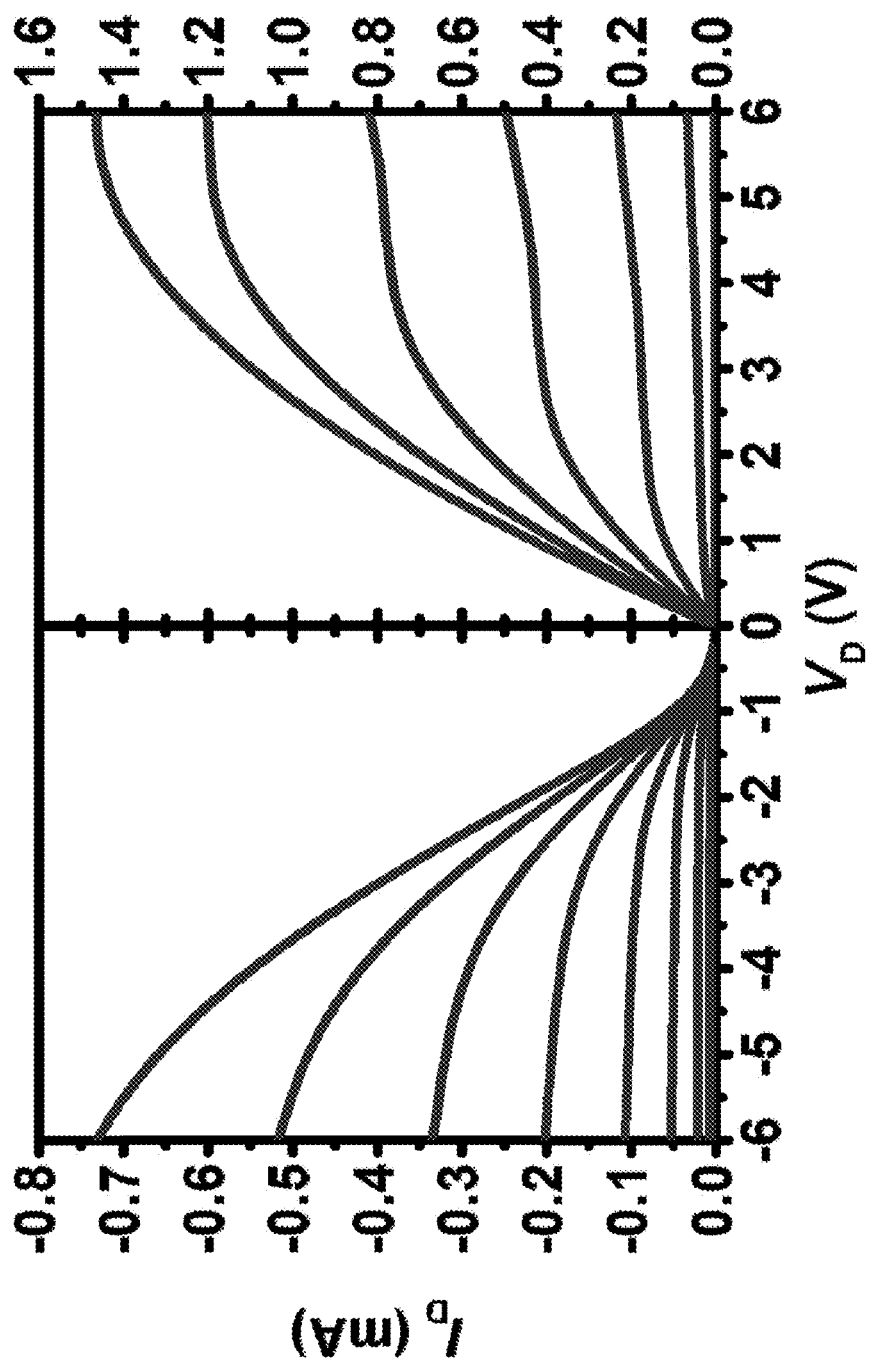
FIG. 24. $I_D$ versus $V_D$ plot of a p-type MOSFET (left) and an n-type MOSFET (right) at $V_G$ steps of 1 V.
Figure 25:
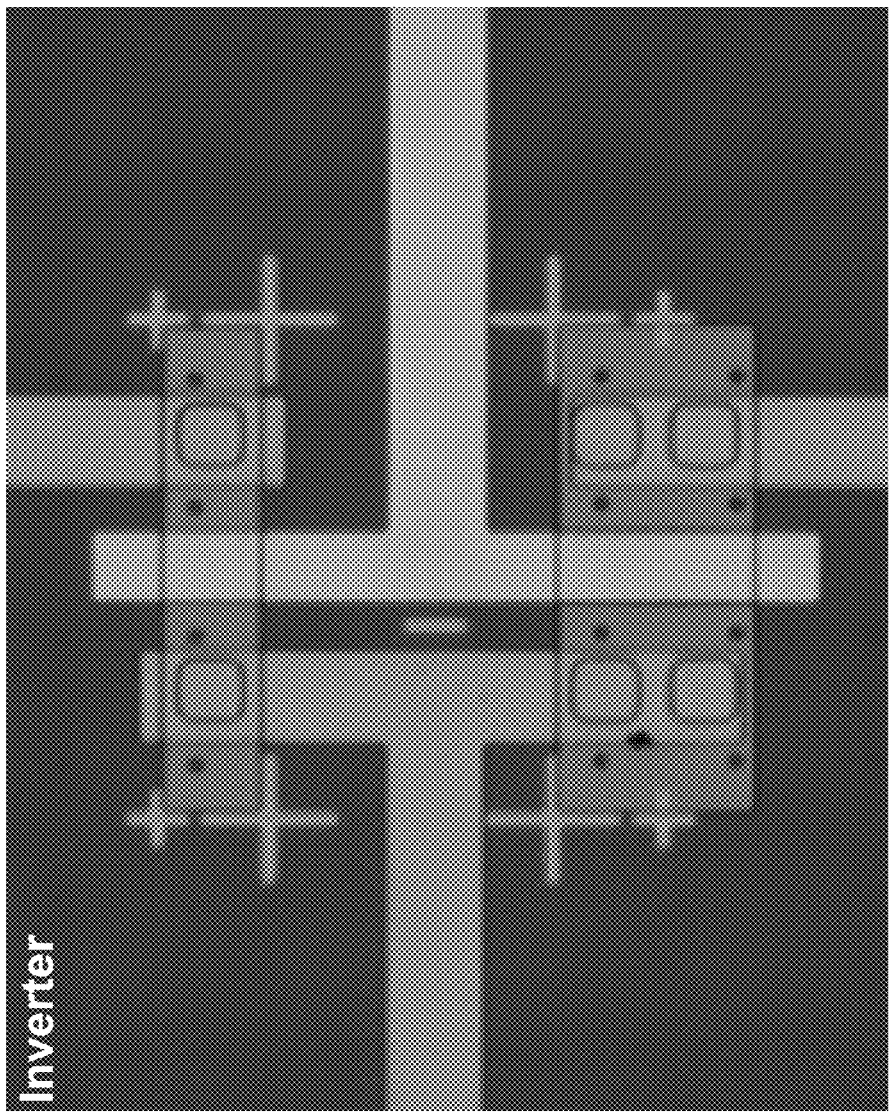
FIG. 25. An optical microscopy image of an inverter.
Figure 26:
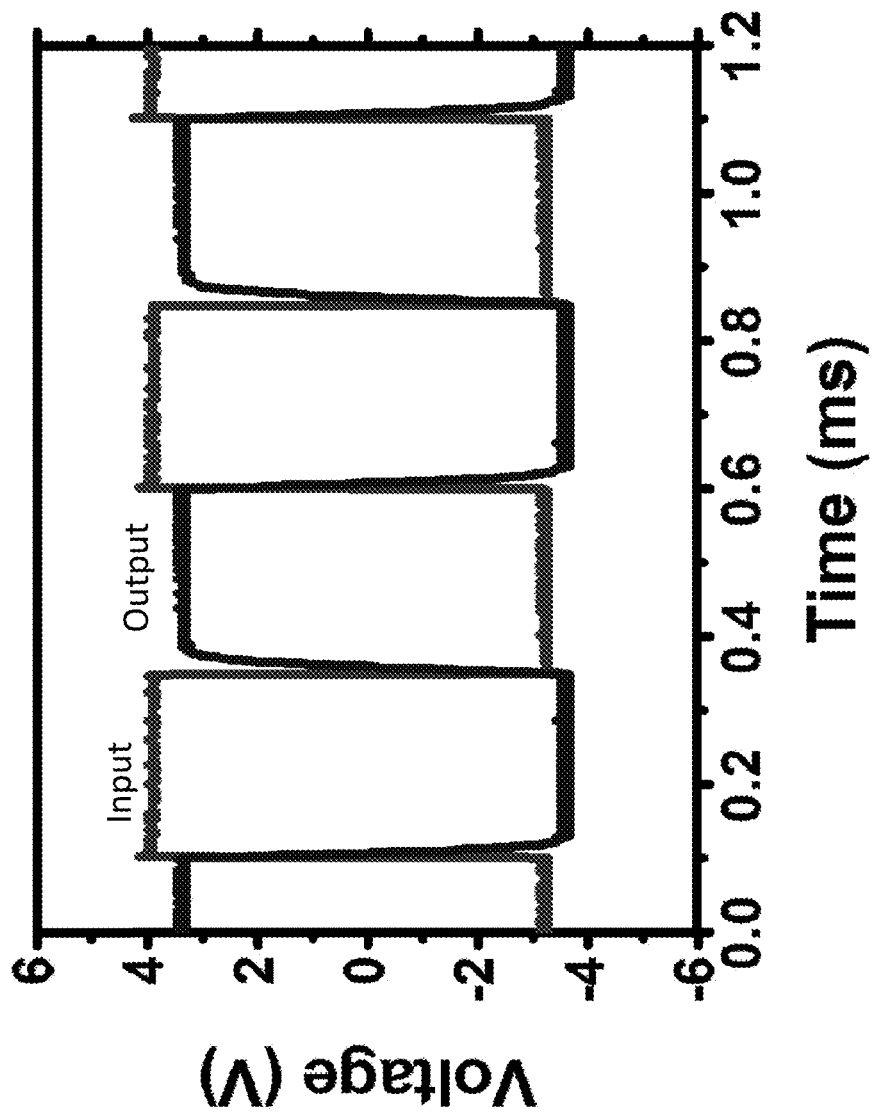
FIG. 26. Input-output characteristics of the inverter.
Figure 27:
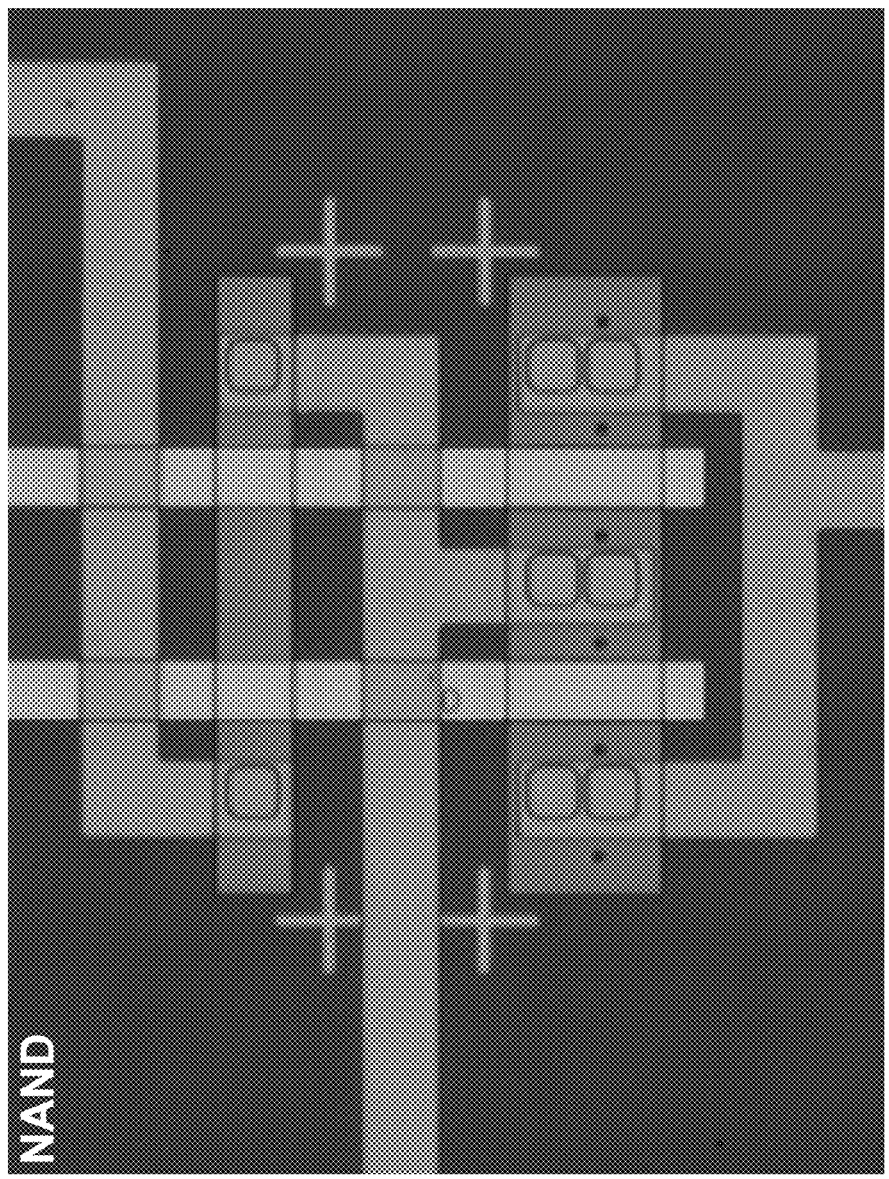
FIG. 27. An optical microscopy image of a NAND gate.
Figure 28:
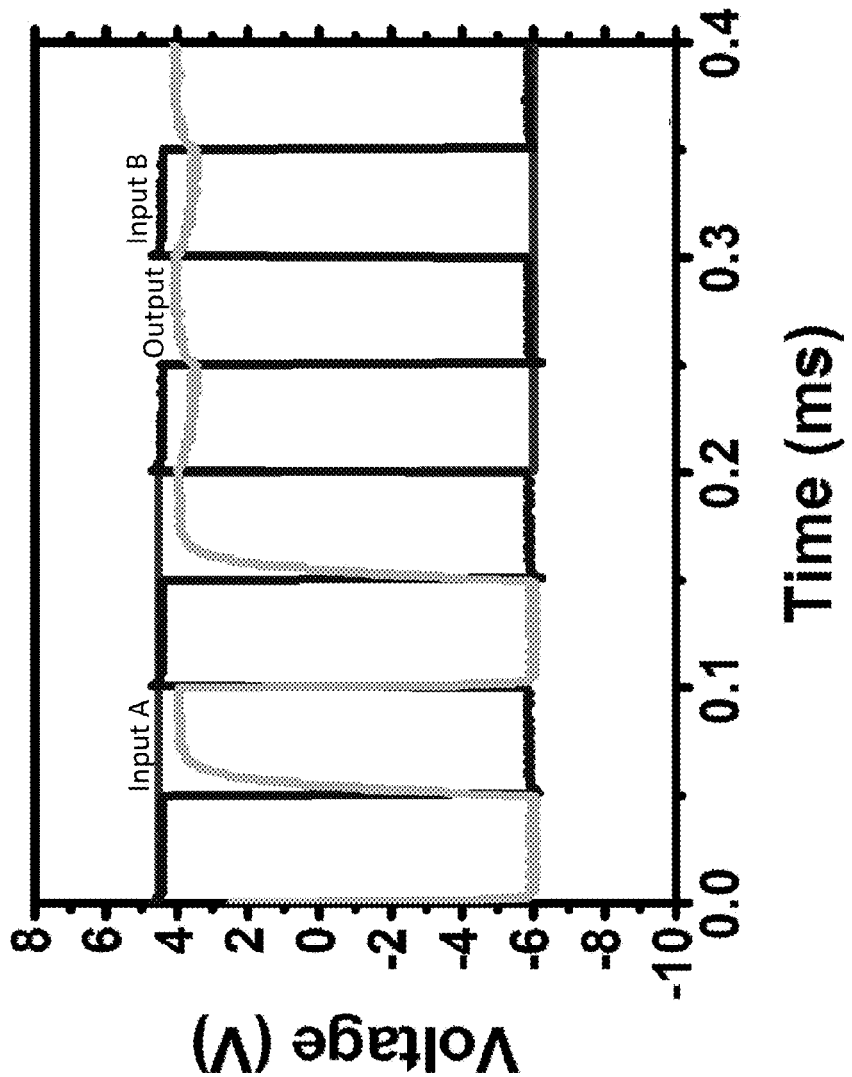
FIG. 28. Input-output characteristics of the NAND gate.
Figure 29:
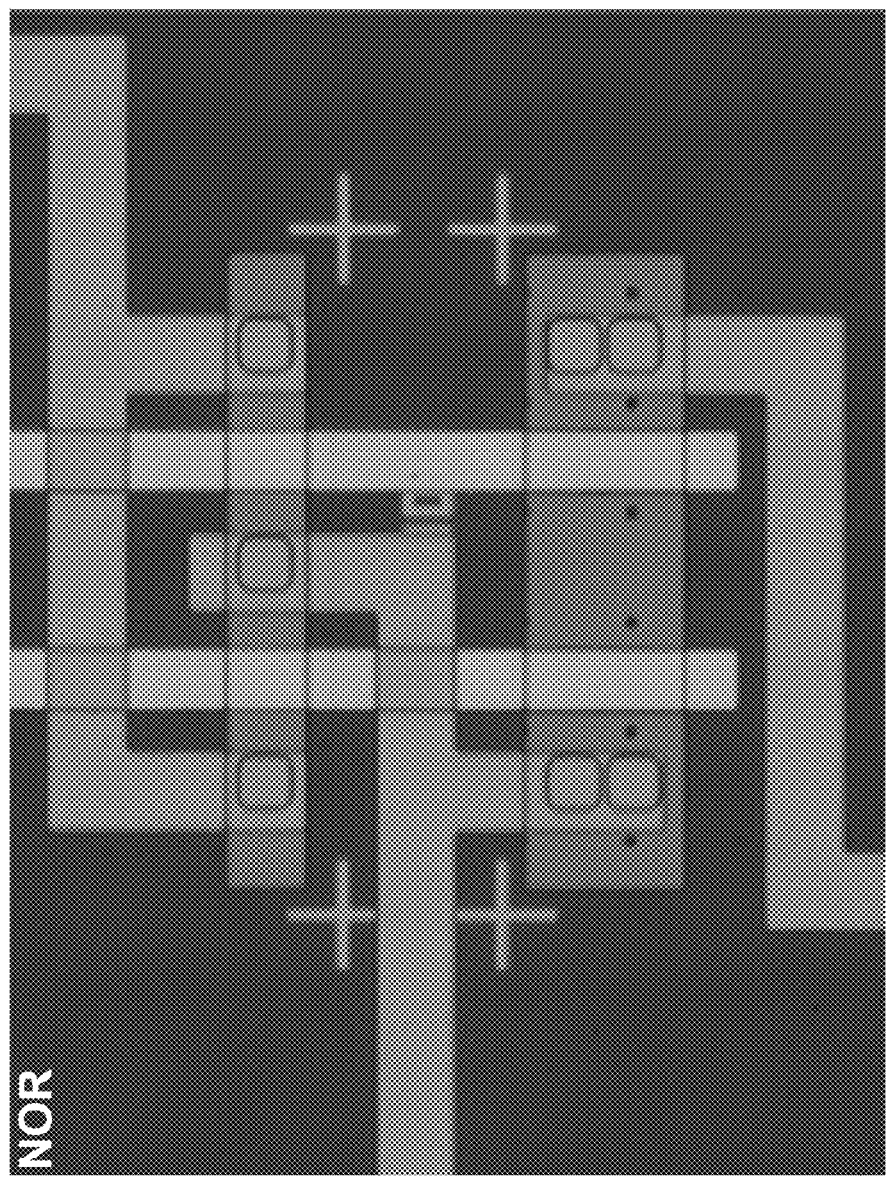
FIG. 29. An optical microscopy image of a NOR gate.
Figure 30:
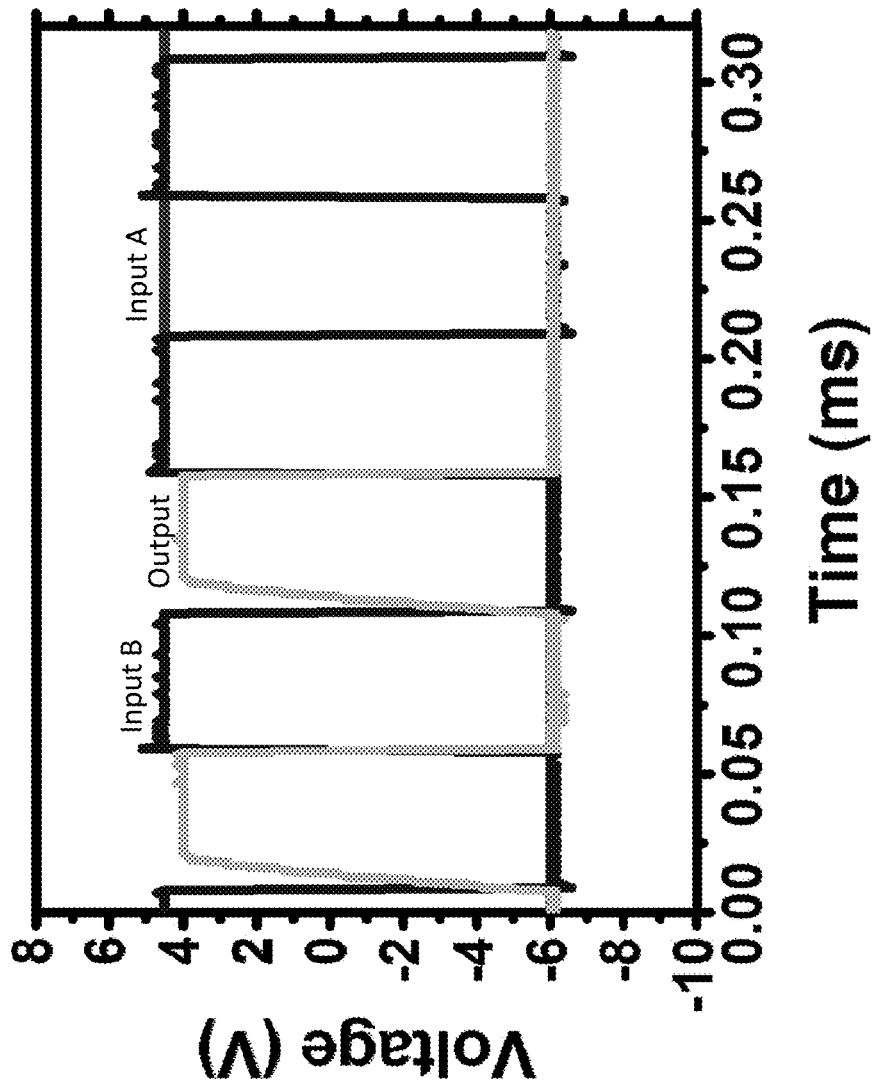
FIG. 30. Input-output characteristics of the NOR gate.
Figure 31:
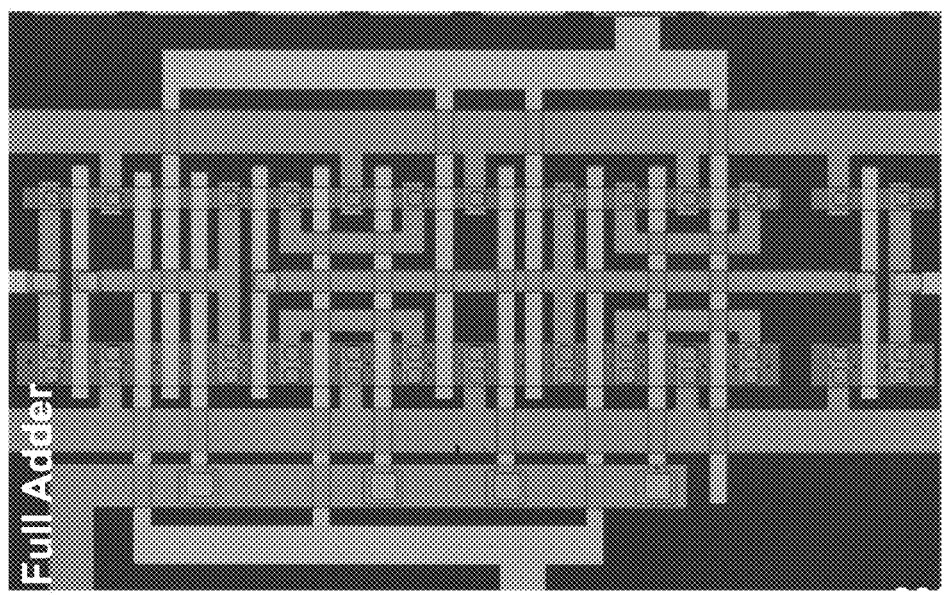
FIG. 31. An optical microscopy image of a full adder. The adder includes of 28 transistors.
Figure 32:
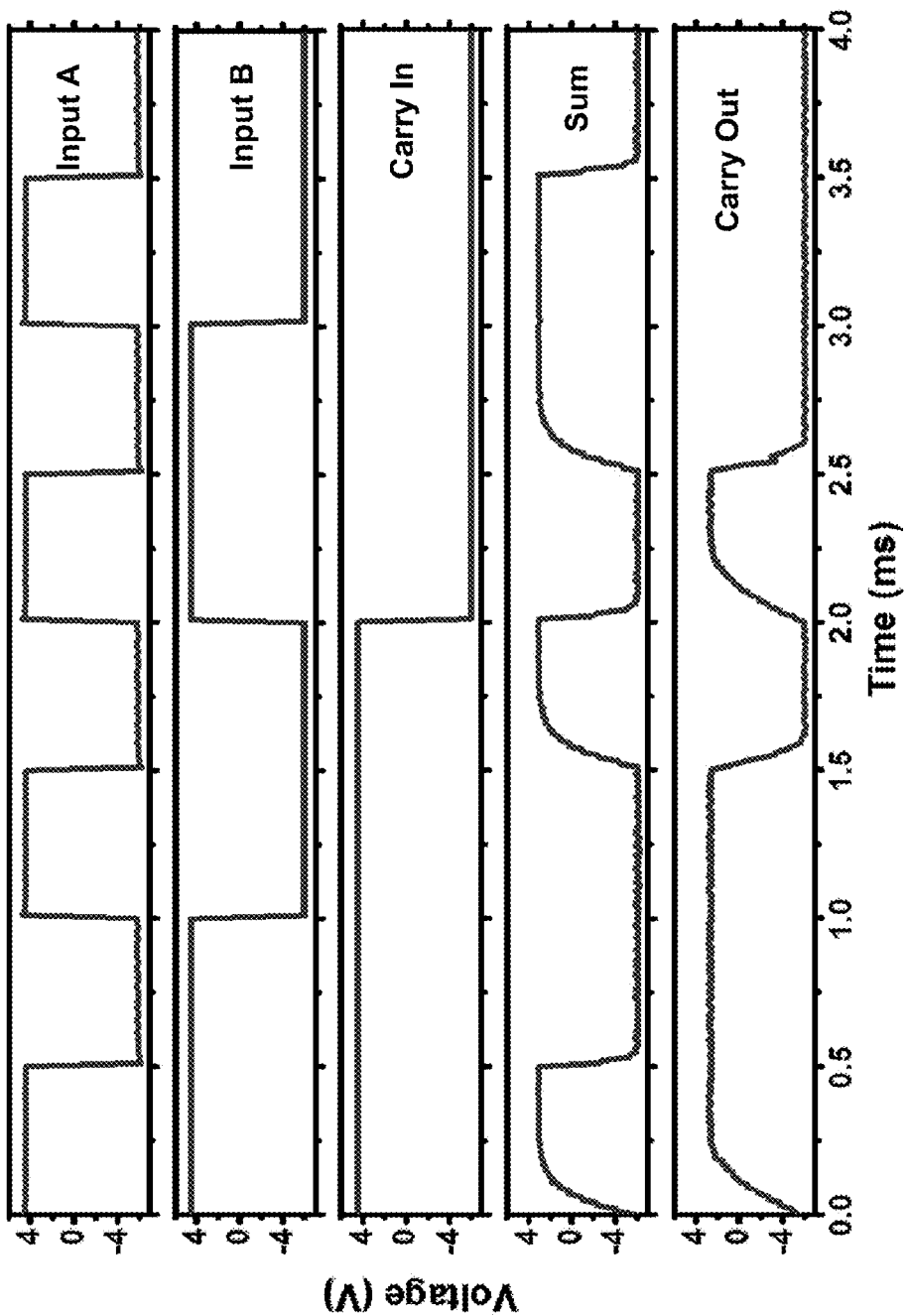
FIG. 32. Characteristics of the full adder: Input A, Input B, Carry In, Sum, and Carry Out are shown in descending order.

In addition to microwave electronics that allow wireless communication for mobile electronic devices, digital circuits are also important components that are dominant in most electronic devices as microprocessors and controllers. FIGS. 24-32 summarize a set of digital logic circuitries on a CNF substrate using Si-based complementary metal-oxide-semiconductor (CMOS) devices. The completed digital circuits on a CNF substrate include 'universal' logic gates (Inverter, NOR gate, and NAND gate) and a full adder. The fabrication was done by separately printing Si nanomembrane-based p-type metal-oxide-semiconductor field-effect transistors (MOSFETs) and n-type MOSFETs onto a polyimide-coated temporary Si substrate, followed by deposition of gate oxides and metal interconnects for making CMOS-based digital circuits. FIG. 24 presents the current-voltage characteristics of the p-type MOSFET (left) and n-type MOSFET (right). FIG. 25 shows an optical image of the CMOS inverter. As presented in FIG. 26, the inverter exhibits a good input and output relationship. A further modeling of these CMOS transistors established NOR and NAND logic gates, which are optically shown in FIGS. 27 and 29, respectively. The input and output relationships of the NOR and NAND gates are shown in FIGS. 28 and 30, respectively. The inputs and outputs can be seen as well-defined "0"s and "1"s. All of these components can be used together to yield a simple integrated circuit on a CNF substrate. As an example, a full adder, which is highly scalable and useful in many cascaded circuits, was designed and fabricated on a CNF substrate, as optically shown in FIG. 31. This full adder is a mirror full adder, which comprised of 28 transistors with 4 of them used for inverter construction. As presented in FIG. 32, the two single bit outputs (SUM and Carry Out) had a 0.2 ms switching delay when responding to the three single bit inputs (Input A, Input B, and Carry In). This made the full adder work at a frequency of up to 5 kHz.

Fungal Biodegradation Tests of the CNF-Based Electronics

Figure 33:
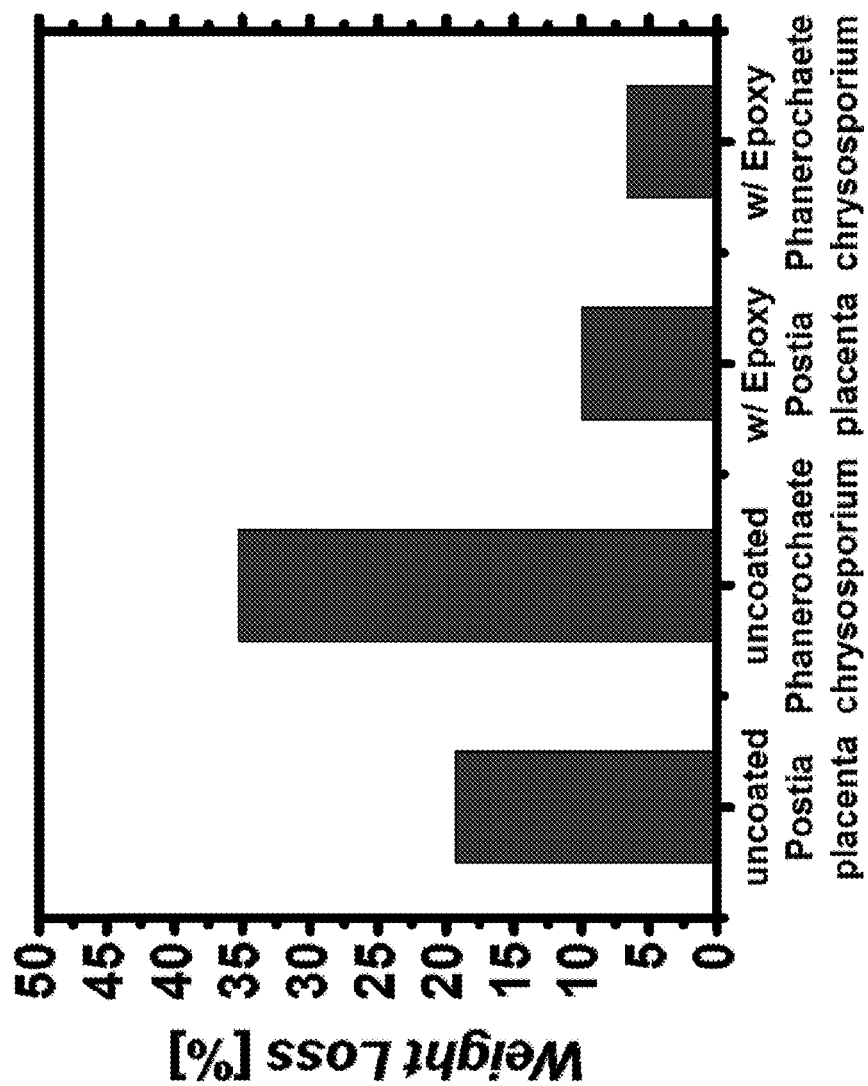
FIG. 33. Fungal biodegradation tests of two types of CNF films. The left two bars show the percent weight loss for uncoated pure CNF films. The right two bars show percent weight loss for epoxy coated CNF films.
Figure 34:
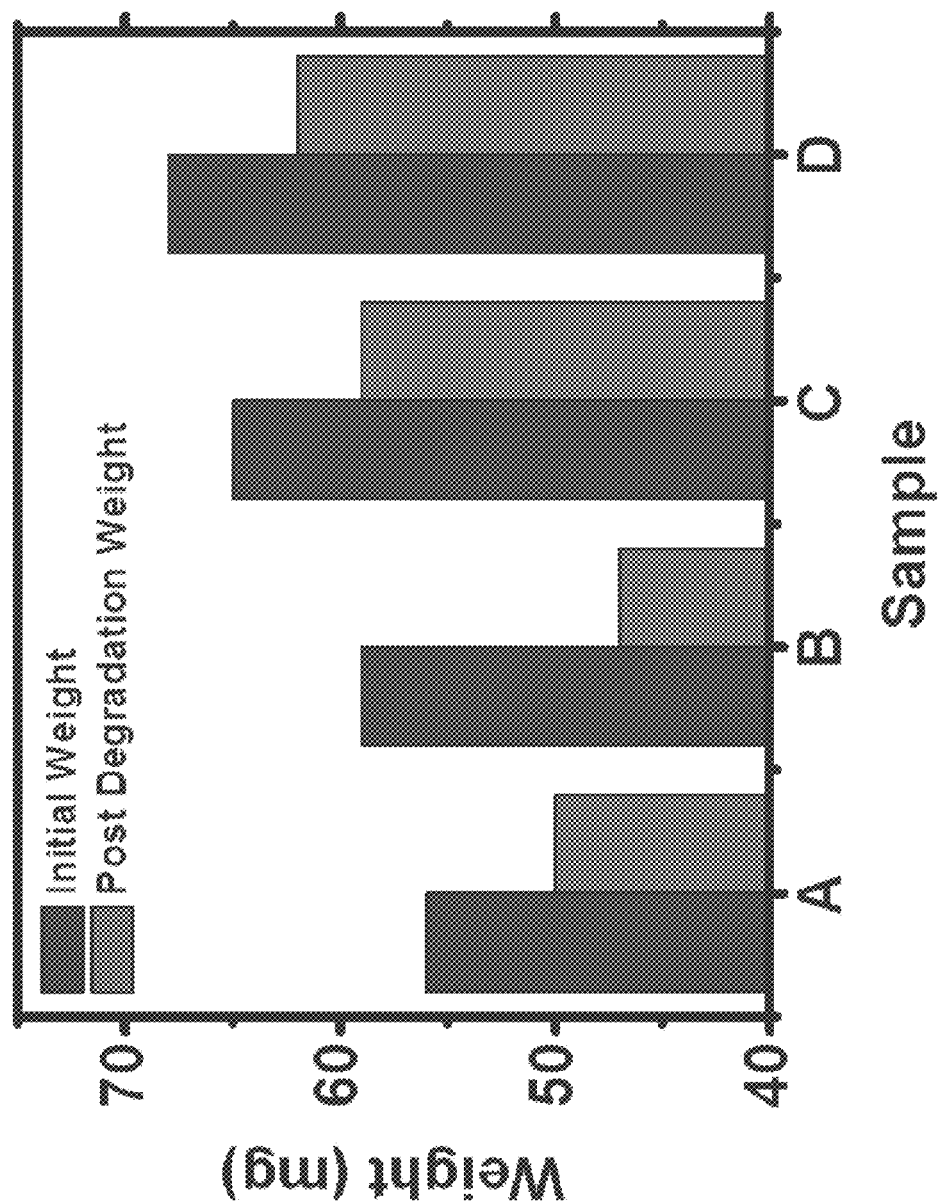
FIG. 34. Fungal biodegradation tests of digital electronics printed on top of the epoxy coated CNF films. Four samples were degraded with *Postia placenta*.
Figure 35:
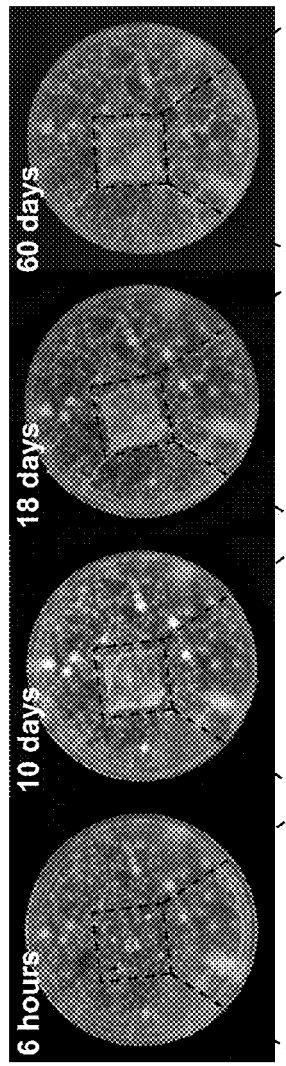
FIG. 35. A series of images taken at 6 hours, 10 days, 18 days, and 60 days after starting the degradation process.
Figure 36:
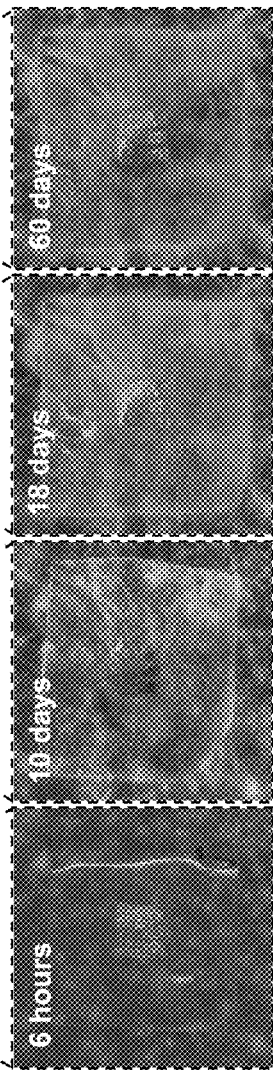
FIG. 36. A series of magnified images of the CNF-based electronics during the degradation process.
Figure 37:
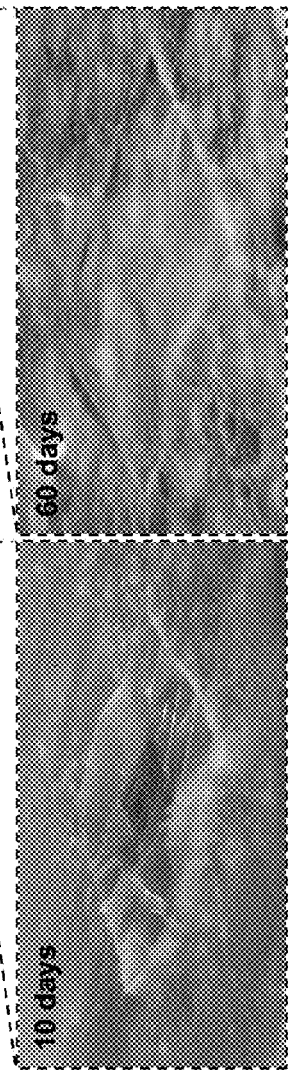
FIG. 37. Tilted view images of the CNF-based electronics after 10 days and 60 days of degradation.

As presented in FIGS. 5-32, all types of electronic systems required for building an electronic device can be realized on a CNF film. To prove the concept of biodegrading electronic devices and to close the cycling loop, one of the electronic-devices presented here was subjected to a fungal degradation test. FIG. 33 summarizes a sequence of fungal degradation tests on CNF-based electronic devices. First, two different types of decay fungi, brown rot fungus *Postia placenta* and white rot fungus *Phanerochaete chrysosporium*, were considered and tested on the pure CNF substrate and on the epoxy-coated CNF substrate, without any electronics printed on them. FIG. 33 presents the average weight loss percentages of these CNF-based films after 28 days. For each degradation test, five identical samples were degraded under the same conditions. Pure CNF samples showed a larger average weight loss (*Postia placenta:* 19.20%, *Phanerochaete chrysosporium:* 35.20%) compared to the epoxy-coated samples. While *Postia placenta* induced a slower degradation rate for pure CNF film, it caused a faster degradation for the epoxy-coated CNF film (*Postia placenta:* 9.96%, *Phanerochaete chrysosporium:* 6.60%) in comparison with *Phanerochaete chrysosporium*. Therefore, *Postia placenta* was chosen as the decaying agent for the CNF-based electronics that consisted of the epoxy-coated CNF film. The amount of epoxy in the epoxy-coated CNF film was 9.6% by weight. FIG. 34 shows the weight loss result of digital electronics on CNF substrates after *Postia placenta* decaying for 84 days. Four replicas were made, and on average, the weight loss percentage was 12.25%, with a standard deviation of 5.43%, suggesting that the CNF film will fully degrade after an extended period of time. FIGS. 35-37 show the images of the decaying process of an epoxy-coated CNF substrate with digital electronics against *Postia placenta*. Photos were taken after 6 hours, 10 days, 18 days, and 60 days as shown in FIGS. 35 and 36. As presented in FIG. 37, the fungi started to partially cover the sample after 10 days, and fully covered the sample after 60 days. Once degraded, the leftover electronics portion, which is encapsulated in polyimide, can be collected to be further decomposed and recycled. Although polyimide can deteriorate with certain fungi, the degradation process is extremely slow compared to CNF, and because polyimide is generally non-permeable to water or solvents, it can be used to protect against any leakage of materials to the environment.

Discussion

In summary, the feasibility of a sustainable, green chip concept that is applicable in both microwave and digital electronics, by strategically combining the minimum use of expensive, environmentally toxic semiconductor materials and the employment of microwave compatible, biodegradable CNF as substitutional substrates, was established. The demonstrated excellent performance GaAs-based HBTs and Schottky diodes, passive inductors and capacitors, and Si-based CMOS digital devices, "universal" logic gates and integrated full adders on CNF substrates, which are essential components in most typical electronic systems, share common fabrication techniques that can be easily integrated together. The combination of all of these thin-film form components into large scale integrated circuits on CNF substrates would provide ways to make many types of fully functional and ecofriendly electronics that could help reduce the accumulation of the massive amounts of persistent electronic waste disposed of daily and dramatically reduce the consumption of non-renewable natural resource.

Methods

Preparation of CNF Substrate:

The tetramethylpiperidine-1-oxy (TEMPO) oxidized CNFs were refined in a microfluidizer processor (Microfluidics, Newton, Mass.), followed by filtering (Millipore Corporation, USA) under air pressure (0.55 MPa) with polytetrafluoroethylene (PTFE) membranes that have 0.1 µm pore sizes. Subsequently, the filter cake was separated from the membrane and sandwiched between layers of waxy coated paper, filter paper, and caul plates at room temperature for drying, followed by further drying in an oven at 60° C. for several hours. The dried CNF film was then coated with a bisphenol A based epoxy resin (Dow Chemical Company, 56:24:24 mixture of low viscosity epoxy resin, flexible epoxy resin, and amine-based curing agent) and pressed at 130° C. for ten minutes under a pressure of 100 psi.

Characterization of CNF Substrate:

A contact angle goniometer (OCA 15/20, Future Digital Scientific Corp., USA) was used for the water contact angle measurements at ambient temperature. The volume of the water droplet was fixed at 4.0 μL, and the contact angle was determined 1 s after the water droplet was deposited on the surface of the CNF film. Three point flexural tests were conducted using a dynamic mechanical analyzer (DMA, TA Instruments RSA III, USA). Rectangular epoxy-coated CNF film (with a length of 40 mm, a width of 13 mm, and a thickness of 0.2 mm) was used for the flexural tests. The maximum flexural deflection was set at 5 mm for the tests. To measure transmittance, CNF film with a thickness of either 80 μm or 200 μm was loaded onto a spectrophotometer (5000 UV-Vis-NIR, Cary). The system was set to transmission mode and the transmittance was recorded every 1 nm throughout the spectrum from 400 nm to 800 nm. The thermal stability of the epoxy coated CNF films were characterized via thermogravimetric analysis (TGA) using a TGA/Q50 thermal analyzer (TA Instruments, DE USA). Approximately 10 mg of the CNF films were heated from 30 to 600° C. at a heating rate of 10° C. $min^{-1}$ in an $N_2$ atmosphere. Differential scanning calorimetry (DSC) was performed in an $N_2$ atmosphere using a DSC thermal analyzer (Auto Q20, TA Instruments) from 0 to 160° C. at a heating rate of 5° C. $min^{-1}$ and a $N_2$ flow rate of 20 mL $min^{-1}$. The sample (~8.0 mg) was stored in a sealed aluminum pan. To measure the electrical breakdown characteristics, metal (Ti/Au, 10/200 nm) was evaporated on both sides of a 200 μm thick CNF film via a shadow mask, with a pad of 300 μm in diameter. High voltage was applied using a voltage source (2410 High-Voltage Source Meter, Keithley) through standard DC probing while the current was monitored. To measure the dielectric constant and loss tangent, the microstrip transmission line-approximation-method was used. A square CNF film with an area of 17.64 $cm^2$ was attached with a copper film as the ground on the back side, and a 6 mm wide copper tape as the transmission line on the center of the top side. S-parameters were collected through the SMA connectors as the RF signal was transmitted through the microstrip transmission line. The dielectric constant and loss tangent of the CNF film were then extracted according to the small signal circuit approximation.

Fabrication of High Speed GaAs HBTs:

The fabrication process began by depositing emitter finger metals (Pd/Ge/Au, 30/40/200 nm) using an electron-beam evaporator via a photoresist (AZ5214) lift-off process, followed by inductively coupled etching (ICP-RIE, $BCl_3$/Ar=10/5 sccm, pressure=2 mTorr, plasma power=50 W, inductor power=500 W) of the cap and emitter layer. Another photoresist lift-off process to deposit base metal fingers (Ti/Pt/Au=10/30/200 nm) and ICP-RIE etching using $SiO_2$ (800 nm) as a hard mask were carried out next to etch the sub-collector layer. After depositing collector metal fingers (Pd/Ge/Au=30/40/200 nm), the sample was annealed at 450° C. for 30 seconds in ambient forming gas ($H_2/N_2$=5/95%) in a rapid thermal anneal (RTA) system for ohmic contact formation. Isolation of individual devices was done using ICP-RIE to etch the sub-collector layer and the underlying sacrificial layer. Protective anchors were patterned by spin casting a thick (~7.0 μm) photoresist layer (Megaposit SPR220, Rohm and Haas Electronic Materials) at 4000 rpm for 30 seconds, soft baked at 110° C. for 120 seconds, exposed to ultra-violet light at a dose of 500 mJ $cm^{-2}$, developed (MF-24A) for 120 seconds, and hard baked at 110° C. for 10 minutes. The AlGaAs sacrificial layer was undercut etched using diluted HF (1:100=deionized water: 49% HF) for 3 hours.

Fabrication of GaAs Schottky Diodes:

A hard mask of $SiO_2$ (800 nm) was deposited via a lift-off process, followed by ICP-RIE etching of an n GaAs layer to reach an $n^+$ GaAs layer. Cathode metal (Pd/Ge/Au=30/40/200 nm) was deposited next via a lift-off process and annealed in RTA (same conditions as the HBT RTA process) for ohmic contact formation. A Schottky metal (Ti/Pt/Au=10/30/200 nm) was deposited on an $n^-$ GaAs layer for anode contact, followed by an ICP-RIE isolation process, patterning of the protective anchor, and sacrificial layer etching using the same procedures used for HBTs.

Preparation of the Micro-Stamp:

A pattern of negative photoresist (SU8 50, Microchem, 100 μm) on a Si substrate was prepared for PDMS (Slygard 184, Dow Corning, 10:1 mixture of pre-polymer to curing agent) molding of an 80×80 $μm^2$ elastomer micro-stamp for selective transfer printing of the devices.

Fabrication of GaAs Devices on a Temporary Substrate:

On a Si substrate, a thin layer of sacrificial polymer, i.e., polymethyl methacrylate (950 PMMA A2, Microchem, 60 nm) was spin casted, followed by hard baking at 180° C. for 3 minutes. A thin sheet of polyimide (PI, Sigma-Aldrich, ~1 μm) was spin casted at 5500 rpm for 60 seconds on the top, followed by soft bake at 80° C. for 25 seconds to create adhesion. Using a micro-stamp mounted on a modified mask aligner (MJB-3 aligner, Karl Suss), an HBT or a Schottky diode was transfer printed on the polyimide adhesive and hard baked at 130° C. for 3 minutes. A quick spray of acetone removed the protective anchor on the device, but left the polyimide undamaged. Another thin sheet of polyimide (~1 μm) was spin casted, followed by soft bake at 150° C. for 5 minutes and hard bake at 300° C. for 1 hour in a vacuum oven. Copper (100 nm) was deposited using an electron-beam evaporator with a lift-off process to serve as a hard mask to open via holes for the device contacts, followed by reactive ion plasma etching (RIE, $CF_4/O_2$=2/40 sccm, pressure=300 mTorr, power=200 W) of polyimide and wet etching of a copper mask (Copper Etch APS-100). G-S-G RF pads (Ti/Cu/Ti/Au=10/1800/10/200 nm) were deposited via a lift-off process for DC and RF characterization of the devices.

Fabrication of Passive Devices on a Temporary Substrate:

On a Si substrate with a PMMA sacrificial layer and a thin sheet of polyimide, a bottom inductor metal and capacitor metal (Ti/Au=10/300 nm) were deposited via a lift-off process. Photolithography patterning on the bottom capacitor metal defined the capacitor size, where the dielectric material ($TiO_2$=200 nm) and top capacitor metal (Ti/Au=10/300 nm) were deposited. With polyimide (~1 μm) spin casted, copper (100 nm) served as a hard mask to open via holes for a top spiral inductor metal and a G-S-G interconnect (Ti/Cu/Ti/Au=10/1800/10/200 nm) deposited via a lift-off process.

Fabrication of Microwave Rectifier on a Temporary Substrate:

Both Schottky diodes and MIM capacitors were integrated together by utilizing the same fabrication processes described above for these two types of devices.

Fabrication of Digital Electronics on a Temporary Substrate:

n-type and p-type active regions for CMOS were prepared separately on the p-type ($4\times10^{15}$ cm$^{-3}$) and n-type ($5\times10^{14}$ cm$^{-3}$) silicon-on-insulator (SOI) wafers. Before ion implantation, 20 nm of thermal oxides (Tystar Oxidation Furnace) were grown on both n- and p-type SOIs for screen oxides. Uniform ion implantation was followed to slightly raise the doping concentration of the active region to minimize channel resistances and adjust the threshold voltage of the MOSFET. A short period of thermal annealing in a furnace was applied to recover the defects generated from implantation and activate the dopants. Heavy ion implantation was applied on the photolithography pre-defined source and drain region. After a second thermal annealing in the furnace, active regions on the SOI wafers were isolated using reactive plasma etching (Unaxis 790). The SOI wafers were then placed in a diluted HF (1:10) solution to etch the sacrificial buried oxide layer and release the membrane. Polyimide (~1 μm) was spin casted and cured on a 60 nm thick PMMA-coated Si wafer. A soft bake of 1 min at 100° C. dried out the solvent while maintaining the adhesive surface. Individually released membranes from each type of the SOIs were aligned and transferred separately onto the polyimide using a PDMS stamp mounted on a modified mask aligner, followed by hard bake at 300° C. for 1 hour in a vacuum oven. A standard source/drain metal pad, dielectric layer, via hole openings, and gate process for CMOS fabrication were processed on a temporary substrate. A second polyimide layer was coated on the surface for passivation and protection followed by via hole etching for the measurement pads.

Transfer Printing Electronics on a CNF Substrate:

The polyimide encapsulated devices (HBT, Schottky diode, inductor and capacitor, and digital electronics) on temporary Si substrates were boiled in acetone at 200° C. for two hours to remove the underlying sacrificial layer (PMMA). A large PDMS elastomer stamp was used to transfer print the finished devices onto the CNF substrate with a thin layer of polymer (SU8 2000.5, Microchem, 500 nm) as the adhesive layer to ensure good bonding between the CNF substrate and the transferred devices.

Measurement and Analysis:

An Agilent N5225A PNA Network Analyzer was used to measure the S-parameter of the microstrip transmission line based on a CNF film. For the devices, the DC measurements were performed using an HP 4155B Semiconductor Parameter Analyzer, and RF measurements were performed using an Agilent E8364A PNA Series Network Analyzer. The measurement setup of the network analyzer was calibrated to the G-S-G probe tips using a standard Short-Open-Load-Thru (SOLT) calibration kit. HP 8350B Sweep Oscillator and 83592B RF Plug-in systems were used to provide RF power to the rectifier. The DC output signals were measured using a Rigol DS 1102E oscilloscope with a 10 ohm resistor as the load. The S-parameters obtained from the RF measurements were analyzed using the Advanced Design System (ADS) software.

Fungal Biodegradation Tests of CNF-Based Electronics:

To prepare for a fungal degradation test, the two decay fungi, *Postia placenta* (Fr.) M. Lars. and Lomb. (MAD 698) and *Phanerochyte chrysosporium* (ME461) were grown and maintained on 2% malt agar (DifCo, Detroit, Mich.) in petri dishes (15×100 mm). Inoculum was incubated at 27° C. in a 70% relative humidity (RH) room for 2 weeks to obtain confluent growth on petri dishes. Meanwhile, the CNF films or CNF-based electronics went through a 24 hour cleaning process in a propylene gas chamber. The cleaned samples were then laid on agar plates containing the confluent fungal growth according to American Wood Preserver's Association E-10-06 standard. Evaluations were observed at 6 hours, 10 days, 18 days, and 60 days for fungal growth on specimens; photographic records were obtained. Photographs were taken at time zero as a control.

Weight Loss Determination of Degraded CNF Substrate:

Pure CNF and epoxy coated CNF substrate specimens either with or without electronics were preconditioned in a 27° C., 65% RH conditioning room for two weeks. The weights were measured and recorded as the initial weight. Thereafter, specimens were loaded in petri dishes, allowing fungal growth and degradation in a 27° C., 70% RH room. At the end of 84 days (28 days for samples without electronics), specimens were harvested, fungal mycelia was brushed off, air dried for 48 hours, and reconditioned for 14 days. Weights were then measured and recorded as post degradation weight. Weight losses were then calculated and determined.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A microwave integrated circuit comprising:
   microwave integrated circuitry comprising active components and passive components, wherein at least one of the active components comprises a Group III-V semiconductor; and
   a biodegradable, dielectric integrated circuit substrate in contact with one or more of the active and passive components;
   wherein the integrated circuit substrate comprises an optically transparent film comprising cellulose nanofibrils and a hydrophobic polymer coating.

2. The integrated circuit of claim 1, wherein the integrated circuit substrate has an RF loss tangent of no greater than 0.045 across the frequency range of 1 to 10 GHz.

3. The integrated circuit of claim 2, wherein the integrated circuit substrate has a dielectric constant of no greater than 3 across the frequency range of 1 to 10 GHz.

4. The integrated circuit of claim 1, comprising no greater than 25 wt. % of non-biodegradable materials.

5. The integrated circuit of claim 1, wherein the active and passive components in the integrated circuit do not include any non-biodegradable dielectric substrates.

6. The integrated circuit of claim 1, wherein the at least one active component comprises a bipolar transistor, a Schottky diode, or both; the Group III-V semiconductor is GaAs, GaInP or InP; and the active components do not include a semi-insulating GaAs substrate.

7. The integrated circuit of claim 6, wherein the integrated circuit is a microwave rectifier circuit or a microwave amplifier circuit.

8. The integrated circuit of claim 1, wherein the Group III-V semiconductor is GaAs and the hydrophobic polymer is an epoxy polymer.

9. The integrated circuit of claim 1, wherein the active and passive components are encapsulated in a polymer that is substantially insoluble in water.

10. The integrated circuit of claim 9, wherein the Group III-V semiconductor is GaAs, the hydrophobic polymer is an epoxy polymer and the polymer that is substantially insoluble in water is a polyimide.

11. The integrated circuit of claim 1, wherein the integrated circuit substrate further comprises electrically insulating particles having a thermal conductivity of at least 30 W/m K.

12. A method of making a microwave integrated circuit, the method comprising:
    forming passive and active components for a microwave integrated circuit on one or more non-biodegradable substrates, wherein at least one of the active components comprises a Group III-V semiconductor;
    releasing the passive and active components from the one or more non-biodegradable substrates; and
    transferring the passive and active components onto a biodegradable, dielectric integrated circuit substrate, such that the passive and active components form the integrated circuitry of the microwave integrated circuit;
    wherein the biodegradable, dielectric integrated circuit substrate comprises an optically transparent film comprising cellulose nanofibrils and a hydrophobic polymer coating.

13. The method of claim 12, wherein the integrated circuit substrate has an RF loss tangent of no greater than 0.045 across the frequency range of 1 to 10 GHz.

14. The method of claim 13, wherein the integrated circuit substrate has a dielectric constant of no greater than 3 across the frequency range of 1 to 10 GHz.

15. The method of claim 12, wherein the integrated circuit comprises no greater than 25 wt. % of non-biodegradable materials.

16. The method of claim 12, further comprising encapsulating the active and passive components in a polymer that is substantially insoluble in water.

17. The method of claim 12, wherein the Group III-V semiconductor is GaAs and the hydrophobic polymer is an epoxy polymer.

* * * * *